US008414684B2

(12) United States Patent
Liu et al.

(10) Patent No.: US 8,414,684 B2
(45) Date of Patent: Apr. 9, 2013

(54) HIGH PRESSURE DEGAS ASSEMBLY FOR CHROMATOGRAPHY SYSTEM AND METHOD

(75) Inventors: Yan Liu, Palo Alto, CA (US);
Christopher A. Pohl, Union City, CA (US); Michael McAdams, Los Gatos, CA (US); Hamish Small, Leland, MI (US); Zhongqing Lu, Fremont, CA (US); Milton Liu, San Mateo, CA (US); Khosro Moshfegh, Fremont, CA (US)

(73) Assignee: Dionex Corporation, Sunnyvale, CA (US)

( * ) Notice: Subject to any disclaimer, the term of this patent is extended or adjusted under 35 U.S.C. 154(b) by 319 days.

(21) Appl. No.: 12/791,732

(22) Filed: Jun. 1, 2010

(65) Prior Publication Data
US 2011/0290726 A1    Dec. 1, 2011

(51) Int. Cl.
*B01D 53/22* (2006.01)
*B01D 19/00* (2006.01)

(52) U.S. Cl.
USPC .................. 95/46; 95/82; 96/6; 96/8; 96/10; 96/101; 210/640; 210/656

(58) Field of Classification Search ............... 95/46, 82; 96/4, 8, 10, 101, 6; 210/656, 640, 188, 198.2; 422/70
See application file for complete search history.

(56) References Cited

U.S. PATENT DOCUMENTS

| | | | |
|---|---|---|---|
| 3,897,213 A | 7/1975 | Stevens et al. | |
| 3,920,397 A | 11/1975 | Small et al. | |
| 3,925,019 A | 12/1975 | Hamish et al. | |
| 3,926,559 A | 12/1975 | Stevens | |
| 4,265,634 A | 5/1981 | Pohl | |
| 4,883,958 A | 11/1989 | Vestal | |
| 5,045,204 A | 9/1991 | Dasgupta et al. | |
| 5,100,555 A | 3/1992 | Matson | |
| 5,352,360 A | 10/1994 | Stillian et al. | |
| 5,569,365 A | 10/1996 | Rabin et al. | |
| 5,788,742 A | 8/1998 | Sugimoto et al. | |
| 5,885,332 A | 3/1999 | Gerner et al. | |
| 5,888,275 A | 3/1999 | Hamasaki et al. | |
| 5,980,742 A * | 11/1999 | Saitoh | 95/46 |

(Continued)

FOREIGN PATENT DOCUMENTS
WO    WO 2007/085900 A2    8/2007

OTHER PUBLICATIONS

Novodoff et al., *Efficient Method for Degassing Surfactant Solutions for Polarographic Analysis*, Analytical Chemistry, 1972, vol. 44, No. 1, pp. 202-203.

*Primary Examiner* — Jason M Greene
(74) *Attorney, Agent, or Firm* — Victor E. Johnson

(57) ABSTRACT

A degas assembly including a low pressure fluid channel for carrying a wash fluid at a first pressure, a pressurized channel for carrying eluent including a gas at a second pressure higher than the first pressure, and a degas separator defining a fluid barrier between the low pressure fluid channel and pressurized fluid channel, the separator configured to retain liquid in the pressurized fluid channel and allow gas to flow through the separator to the low pressure fluid channel. The pressurized fluid channel may extend along an outer periphery of the low pressure fluid channel. The eluent may be received from an eluent generator at a pressure of at least about 3300 psi, and in various embodiments up to about 5000 psi. A liquid chromatography system and method are also disclosed.

31 Claims, 16 Drawing Sheets

U.S. PATENT DOCUMENTS

| | | | |
|---|---|---|---|
| 6,030,358 | A | 2/2000 | Odland |
| 6,225,129 | B1 | 5/2001 | Liu et al. |
| 6,312,647 | B1 | 11/2001 | Spears |
| 6,319,398 | B1 | 11/2001 | Saitoh |
| 6,346,142 | B1 | 2/2002 | Jetter et al. |
| 6,350,297 | B1 | 2/2002 | Doyle et al. |
| 6,682,701 | B1 | 1/2004 | Liu et al. |
| 6,805,730 | B2 * | 10/2004 | Herczeg ............... 96/8 |
| 6,837,992 | B2 * | 1/2005 | Gerner et al. ............ 95/46 |
| 6,949,132 | B2 | 9/2005 | Thielen et al. |
| 6,955,922 | B1 | 10/2005 | Liu et al. |
| 7,144,443 | B2 | 12/2006 | Gerner et al. |
| 7,390,386 | B2 | 6/2008 | Srinivasan et al. |
| 7,427,312 | B2 | 9/2008 | Gerner et al. |
| 7,713,331 | B2 | 5/2010 | Gerner et al. |
| 2001/0037731 | A1 * | 11/2001 | Sims et al. ............ 96/6 |
| 2003/0012709 | A1 | 1/2003 | Xu et al. |
| 2003/0116491 | A1 | 6/2003 | Yamazaki et al. |
| 2003/0127392 | A1 | 7/2003 | Srinivasan et al. |
| 2006/0037911 | A1 * | 2/2006 | Dasgupta et al. ........ 210/656 |
| 2006/0057733 | A1 | 3/2006 | Liu et al. |
| 2007/0140916 | A1 * | 6/2007 | Spiss ............... 422/100 |
| 2010/0288024 | A1 * | 11/2010 | Sugiyama et al. ........ 96/6 |

* cited by examiner

HIGH PRESSURE DEGAS ASSEMBLY FOR CHROMATOGRAPHY SYSTEM AND METHOD

FIELD OF THE INVENTION

This invention relates, in general, to a system for high-performance ion or liquid chromatography and in various aspects an apparatus and method for removal of gas from an eluent.

BACKGROUND OF THE INVENTION

Ion chromatography is a common technique for analysis of sample materials. Conventional ion chromatography typically includes a chromatographic separation stage using an eluent containing an electrolyte and an eluent suppression stage followed by detection. In the chromatographic separation stage, analyte ions of interest in an injected sample are eluted through a separation column using an electrolyte as the eluent. In the suppression stage, electrical conductivity of the electrolyte is suppressed while not affecting the separated ions so that the ions may be determined by a conductivity cell. This technique is described in detail in U.S. Pat. Nos. 3,897,213; 3,920,397; 3,925,019 and 3,926,559.

Dilute solutions of acids, bases, or salts are commonly used as chromatographic eluents. Traditionally, these eluents are prepared off-line by dilution with reagent-grade chemicals. Off-line preparation of chromatographic eluents can be tedious and prone to operator errors, and often introduces contaminants. For example, dilute sodium hydroxide (NaOH) solutions, widely used as eluents in the ion chromatographic separation of anions, are easily contaminated by carbonate. The preparation of carbonate-free NaOH eluents is difficult because carbonate can be introduced as an impurity from the reagents or by adsorption of carbon dioxide from air. The presence of carbonate in NaOH eluents can compromise the performance of an ion chromatographic method, and can cause an undesirable chromatographic baseline drift during a hydroxide gradient and even irreproducible retention times of target analytes. In recent years, several approaches that utilize the electrolysis of water and charge-selective electromigration of ions through ion-exchange media have been investigated by researchers to purify or generate high-purity ion chromatography eluents. U.S. Pat. Nos. 6,225,129, 6,682,701, and 6,955,922 describe electrolytic devices that can be used to generate high purity acid and base solutions by using water as the carrier. Using these devices, high purity, contaminant-free acid or base solutions are automatically generated on-line for use as eluents in chromatographic separations. These devices simplify gradient separations that can now be performed using electrical current gradients, with minimal delay, instead of using a conventional mechanical gradient pump.

With conventional electrolytic eluent generators, however, gases can be introduced into the eluent during the electrolytic reaction or at other stages in the analysis process. For example, in a large capacity potassium hydroxide (KOH) generator, electrolysis reactions produce hydrogen and oxygen gases. When used in a chromatography system, the hydrogen gas, along with the KOH solution, is carried forward into the chromatographic flow path. If hydrogen gas is produced in a significant volume relative to the liquid flow, its presence can be detrimental to the detection process and other downstream chromatography processes.

One solution to the problem of a presence of gas in the eluent is disclosed by U.S. Pat. No. 6,225,129 to Liu et al. ("Liu patent"). The Liu patent discloses a method for addressing the potential problem of hydrogen gas by application of Boyle's law. A flow restrictor is placed after the detector flow cell to create backpressure and elevate the pressure of the entire chromatography system. Under elevated pressure (e.g., 1000 psi or higher), hydrogen gas is compressed to an insignificant volume compared to the eluent flow so that it does not interfere with the downstream chromatography process. But this approach has several drawbacks. Because of the elevated pressures, the detector flow cell must be capable of withstanding a pressure of 1000 psi or more. In the case of ion chromatography system using suppressed conductivity detection, the suppressor must also be capable of withstanding an elevated high pressure. Therefore, this approach limits the type of components that can be used in an ion chromatography system employing an electrolytic eluent generator.

Another approach involves using an on-line gas removal device to remove hydrogen gas from the KOH solution. One way to remove the gas from an effluent is to pass the effluent through a gas removal device having a gas diffusion membrane prior to reaching the detection cell. An exemplar of a gas removal device used with a chromatography system is disclosed in U.S. Pat. No. 5,045,204 to Dasgupta et al. ("Dasgupta patent").

The Dasgupta system includes a device for removal of gas (e.g. hydrogen) generated in the electrolytic cell from the product stream (e.g. sodium hydroxide). In one embodiment, the gas removal device is a gas diffusion cell including a plurality of blocks and a gas diffusion membrane separating a degassed product channel from a gas carrier channel. In another embodiment, gas-containing product is directed into a porous hydrophobic tube that is configured for the product to flow downwardly and then upwardly out of an exit port. The tube is formed of hydrophobic materials (e.g. as porous polytetraofluoroethylene (PTFE), (expanded)PTFE, Accurel®, or Celgard®) similar to the membrane. The hydrogen gas flows outwardly through the tube to a gas vent. As the KOH eluent stream passes through the tube under pressure, hydrogen gas diffuses through the tube and is carried to waste. In this manner gas is effectively removed from the eluent before it reaches the sample injector of the chromatography system so that the downstream chromatographic process is not affected. One advantage of this system is that a conventional detector flow cell and ion chromatography suppressor can be used.

The Liu patent discloses a similar gas removal device for on-line removal of gas from the eluent solution. The gas removal device includes a gas-permeable tubing coaxially aligned within a protective tubing. The gas-permeable tubing functions like a membrane. In operation, the KOH solution containing hydrogen gas is pumped through the gas permeable tubing and the hydrogen gas escapes through the tubing. A stream of aqueous solution flowing in an annular space between the outside of the gas permeable tubing and the protective tubing carries away the released gas.

One problem with such conventional gas removal devices is that current gas diffusion materials can not withstand pressures found in modern systems. Ion chromatography systems, in particular high-performance liquid chromatography (HPLC) systems, experience high in-line pressures. Conventional membrane materials have low burst pressures by comparison. By example, typical systems can rise above 1000 psi, and modern pumps can generate pressures in excess of 3000 psi and even 5000 psi. Such pressure levels are above the burst pressure of porous and gas-permeable tubing used for conventional gas removal devices such as those of the Dasgupta and Liu patents. Further, the low pressure threshold of such conventional devices limits the capabilities of the overall system. For example, systems making use of such gas removal devices are limited to about 3000 psi in the separation column. High pressure is desirable for greater efficiency and performance.

One solution to this has been to position the electrolytic eluent generator and the gas removal device on the low pressure side of the system, meaning in the pump intake line, or external (off-line) to the system. However, these positioning solutions limit the effectiveness of the devices and add to the volume of the electrolytic eluent generation system, thus compromising the overall performance of the ion chromatography system.

Thus, there is need to develop a degasser device that can be used in conjunction with an electrolytic eluent generator in ion chromatography and liquid chromatography systems over a wider range of operational pressures. There is a continuing need for chromatography systems with increased efficiency and performance.

In light of the foregoing, it would be beneficial to have methods and apparatuses which overcome the above and other disadvantages of known gas removal devices and chromatography systems.

BRIEF SUMMARY OF THE INVENTION

In summary, one aspect of the present invention is directed to a degas assembly including a low pressure fluid channel for carrying a wash fluid at a first pressure, a pressurized channel for carrying eluent including a gas at a second pressure higher than the first pressure, and a degas separator defining a fluid barrier between the low pressure fluid channel and pressurized fluid channel, the separator configured to retain liquid in the pressurized fluid channel and allow gas to flow through the separator to the low pressure fluid channel.

In various embodiments, the pressurized fluid channel extends along an outer periphery of the low pressure fluid channel. In various embodiments, the second pressure is at least about 3000 psi. In various embodiments, the second pressure is at least about 3300 psi. In various embodiments, the second pressure is between about 3000 psi and about 5000 psi.

In various embodiments, the degas assembly includes a central lumen extending within an outer tubing. The central lumen forms the low pressure fluid channel, an annular space between the central lumen and the tubing defines the pressurized channel, and a wall of the central lumen defines the degas separator. In various embodiments, the pressurized fluid channel extends along substantially the entire outer periphery and substantially the entire length of the low pressure fluid channel.

In various embodiments, the eluent is received from an eluent generator and has a pressure of at least about 3300 psi. In various embodiments, the eluent is received from an eluent generator and has a pressure between about 3300 psi and about 5000 psi.

In various embodiments, the degas assembly further includes a low pressure channel member defining the low pressure fluid channel and a pressurized channel member defining the pressurized fluid channel, each of the channel members comprising inert polymer tubing. The low pressure fluid channel member may include amorphous fluoropolymer tubing. The pressurized fluid channel member may include reinforced polyetheretherketone (PEEK) tubing.

In various embodiments, the degas assembly further includes an inlet housing and outlet housing. The inlet housing may include an eluent inlet for connecting to an eluent generator and a wash inlet for connecting to a wash source. The outlet housing may include an eluent outlet and a wash outlet.

In various embodiments, the low pressure fluid channel is fluidicly connected to the wash inlet and the wash outlet, and the pressurized fluid channel is fluidically connected to the eluent inlet and the eluent outlet. In various embodiments, the low pressure fluid channel and pressurized fluid channel are substantially coaxial flexible tubes. At least one of the low pressure and pressurized tubes may include a splined portion at an outlet end and clamped within the outlet housing. The splined portion may be configured to allow fluid to flow through the splines when the splined portion is clamped. In various embodiments, the splined portion extends along substantially the entire length of the pressurized tube. In various embodiments, the outer tubing has a non-circular cross-section. In various embodiments, an outer surface of the central lumen is non-cylindrical.

Various aspects of the inventions are directed to a liquid chromatography system including a degas assembly and a pressurized liquid chromatography column. In various embodiments, eluent from the outlet housing flows to the column.

In various embodiments, the system further includes a pump, and the degas assembly is positioned downstream from the pump. In various embodiments, the system further includes a pump, and the degas assembly is positioned upstream from an inlet of the pump.

Various aspects of the inventions are directed to a method of separating gas from an eluent for liquid chromatography. The method includes flowing high pressure eluent to a degas assembly, the degas assembly including an inner flow channel and outer flow channel with a degas separator disposed therebetween, said degas separator being a permeable membrane; flowing the eluent to the outer flow channel; and separating gas from the eluent into the inner flow channel but retaining liquid from the eluent in the outer flow channel via the degas separator.

In various embodiments, the eluent includes gas resulting from electrolysis.

In various embodiments, the method further includes directing the separated eluent from an outlet of the outer flow channel to a liquid chromatography column.

In various embodiments, the method further includes flowing regenerant through the inner flow channel thereby flushing the separated gas. In various embodiments, the eluent is received from an eluent generator. In various embodiments, eluent from the eluent generator is at a pressure of at least about 3300 psi. In various embodiments, eluent from the eluent generator is at a pressure of between about 3300 psi and about 5000 psi.

In various embodiments, the degas separator is a polymer tube.

In various embodiments, the outer flow channel at least partially envelops the inner flow channel, and the flowing eluent to the outer flow channel is performed so as to place the inner flow channel in compression.

The apparatus and method of the present invention(s) have other features and advantages which will be apparent from or are set forth in more detail in the accompanying drawings, which are incorporated in and form a part of this specification, and the following Detailed Description of the Invention, which together serve to explain the principles of the present invention(s).

BRIEF DESCRIPTION OF THE DRAWINGS

FIG. 18 shows the poor conductivity profile of the KOH eluents when there is insufficient removal of hydrogen gas in conjunction with a KOH electrolytic eluent generator.

DETAILED DESCRIPTION OF THE INVENTION

Reference will now be made in detail to the various embodiments of the invention, examples of which are illustrated in the accompanying drawings. While the invention will be described in conjunction with the various embodiments, it will be understood that they are not intended to limit the invention to those embodiments. On the contrary, the invention is intended to cover alternatives, modifications and equivalents, which may be included within the spirit and scope of the invention as defined by the appended claims.

Various aspects of the present invention are similar to the devices and systems described in U.S. Pat. Nos. 7,390,386 B2; 6,682,701 B1; 6,225,129 B1; 5,569,365; and 5,045,204 and U.S. Patent Application No. 2003/0127392 A1, the entire contents of which are incorporated herein for all purposes by this reference.

The gas removal assembly and method of the present invention will first be broadly described in combination with an ion chromatographic system. For the analysis of anions on a chromatographic system generally, the eluent is an electrolyte, typically a cation hydroxide such as sodium hydroxide (NaOH). Conversely, for the analysis of cations, the eluent typically is an acid such as methanesulfonic acid (MSA). The gas removal device and method of the present invention, however, are also applicable to liquid chromatography forms other than ion chromatography. The present inventions are also applicable to other gas removal and separation applications including, but not limited to, industrial applications involving gassified fluid streams. An example of use of a conventional gas separation device for gas clean-up and purification of a liquid stream is disclosed by U.S. Pat. No. 6,350, 297, which is incorporated herein for all purposes by this reference.

By "gassified" it is meant that the liquid stream includes a gas component, whether resulting from a prior process or occurring naturally. "Degassed" refers to the resulting product after removal of the gas in accordance with the invention. "Degassed", "degas", and "degasser" are used interchangeably in various respects to refer to the device and resulting product using the device. In various respects, "separated solution" refers to degassed sample solution.

Figure 1:
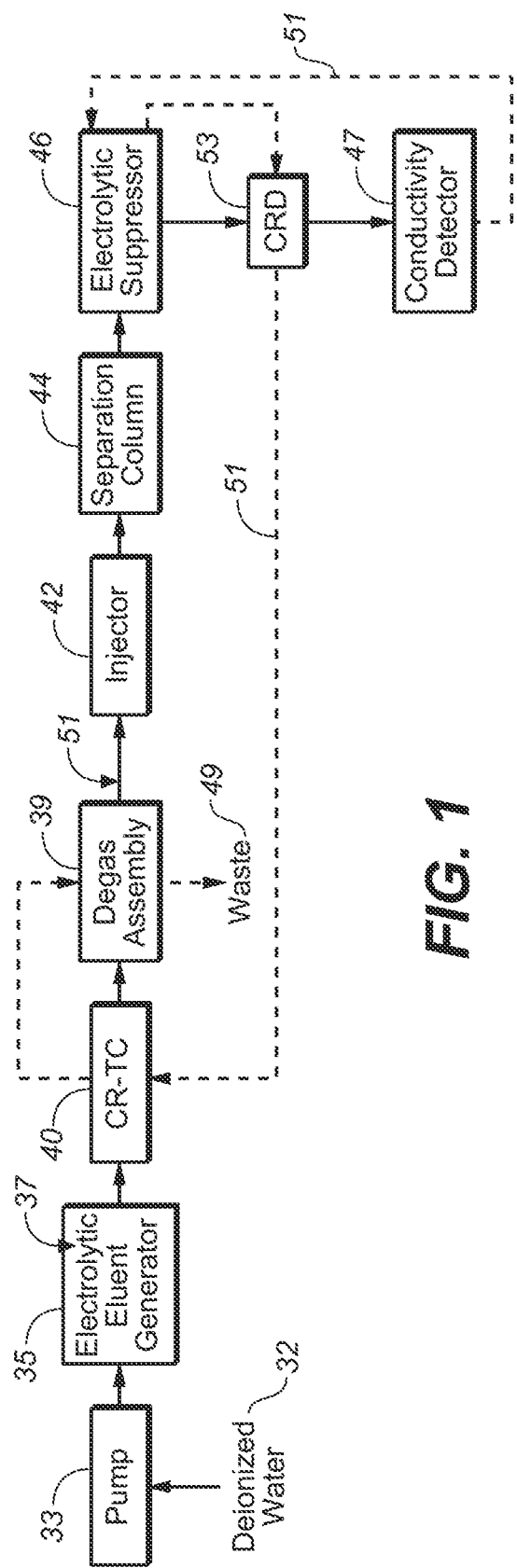
FIG. 1 is a schematic representation of an exemplary system and gas removal apparatus in accordance with the present invention.

FIG. 1 represents an ion or liquid chromatography system 30 in accordance with the present invention. The system feeds a potassium hydroxide (KOH) eluent to a column for analysis of a sample. A stream of deionized water from an eluent source or reservoir 32 is drawn by one or more pumps 33. The pump delivers the water stream to an eluent generator 35, which includes power source 37. An eluent purifier may also be paired with the eluent generator. The exemplary KOH eluent generator includes a high pressure generation chamber containing a platinum (Pt) cathode and a low pressure electrolyte reservoir containing a Pt anode. Under the applied electrical field, the potassium ions migrate across an ion exchange connector to combine with hydroxide ions generated at the cathode to form the KOH eluent. The concentration of KOH solution formed is proportional to the applied current and inversely proportional to the flow rate of the deionized water carrier stream.

In the exemplary system, the eluent flowing from the generator includes a gas component (e.g. hydrogen) as a result of the electrolytic reaction. From the generator, the eluent flows through a degas assembly, generally designated 39, for removal of the gas. The exemplary degas assembly is provided on-line in the system and downstream from the pump, the outlet of the large capacity KOH generator, and an optional continuously-regenerated trap column (CR-TC) 40. The degassed sample is fed to a sample injector 42 for injection into a separation column 44, such as a chromatography column. Thus, hydrogen gas is effectively removed from the KOH eluent before it reaches the sample injector of the chromatography system so that the downstream chromatographic process is not affected.

The exemplary system includes chromatographic separation means in the form of chromatographic column 44 which is packed with a chromatographic separation medium.

In one embodiment, the separation medium is an ion-exchange resin. In one embodiment, the separation medium is a porous hydrophobic chromatographic resin with essentially no permanently attached ion-exchange sites. The resin system may be used for mobile phase ion chromatography (MPIC) as described in U.S. Pat. No. 4,265,634.

The eluate from column 44 is fed to a self-regenerating suppressor 46 similar to those described in U.S. Pat. No. 5,352,360 and of the type sold by Dionex Corporation of Sunnyvale, Calif. under the SRS® name. The suppressor serves to suppress the conductivity of the electrolyte of the eluent from the column but not the conductivity of the separated ions. The suppressor generally converts the electrolyte of the eluent to a weakly conducting form. The suppression process usually enhances the conductivity of the separated ions.

With continued reference to FIG. 1, the effluent from suppressor 46 is directed to a detector 47, such as a flow-through conductivity cell, for detecting the resolved ionic species. In the detector, the presence of ionic species produces an electrical signal proportional to the amount of ionic material. The output signal is typically directed from the detector to a conductivity meter thereby permitting detection of the concentration of separated ionic species.

Recycled aqueous liquid from detector 47 may be utilized as a regenerant solution. In various embodiments, the regenerant from the suppressor is used as a wash fluid to carry separated gas from degas assembly 39 to a waste receptacle 49. The regenerant solution from exemplary detector 47 flows in a fluid line, generally designated 51, and serves as the solution to carry away the removed gas from the degas assembly so that the system can be operated continuously. The recycled liquid may be directed to the degas assembly directly or via other components. An optional carbonate removal device (CRD) 53 is positioned between the suppressor and detector.

Figure 2:
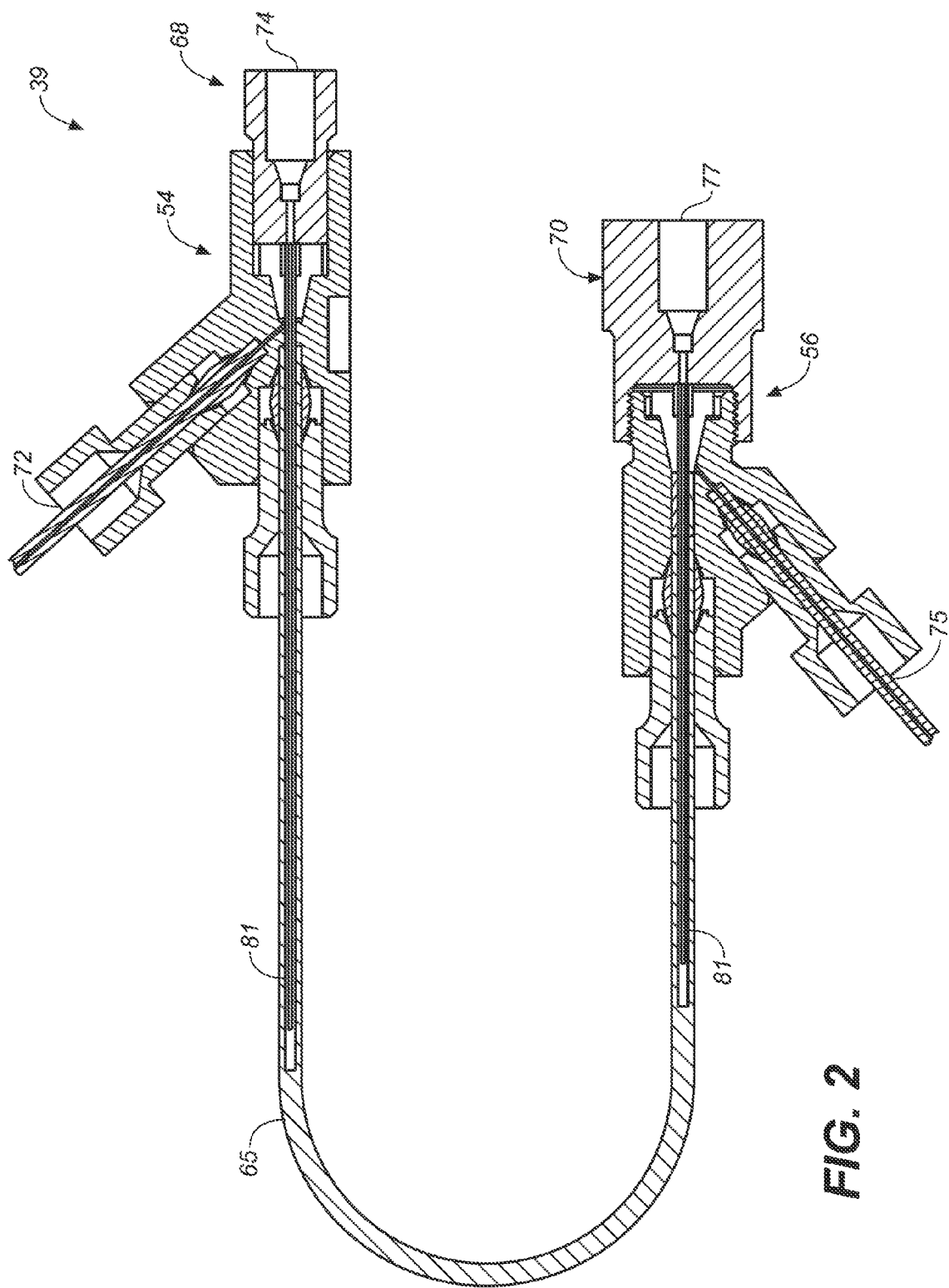
FIG. 2 is a cross-sectional view of an exemplary gas removal assembly used with the system of FIG. 1.
Figure 3:
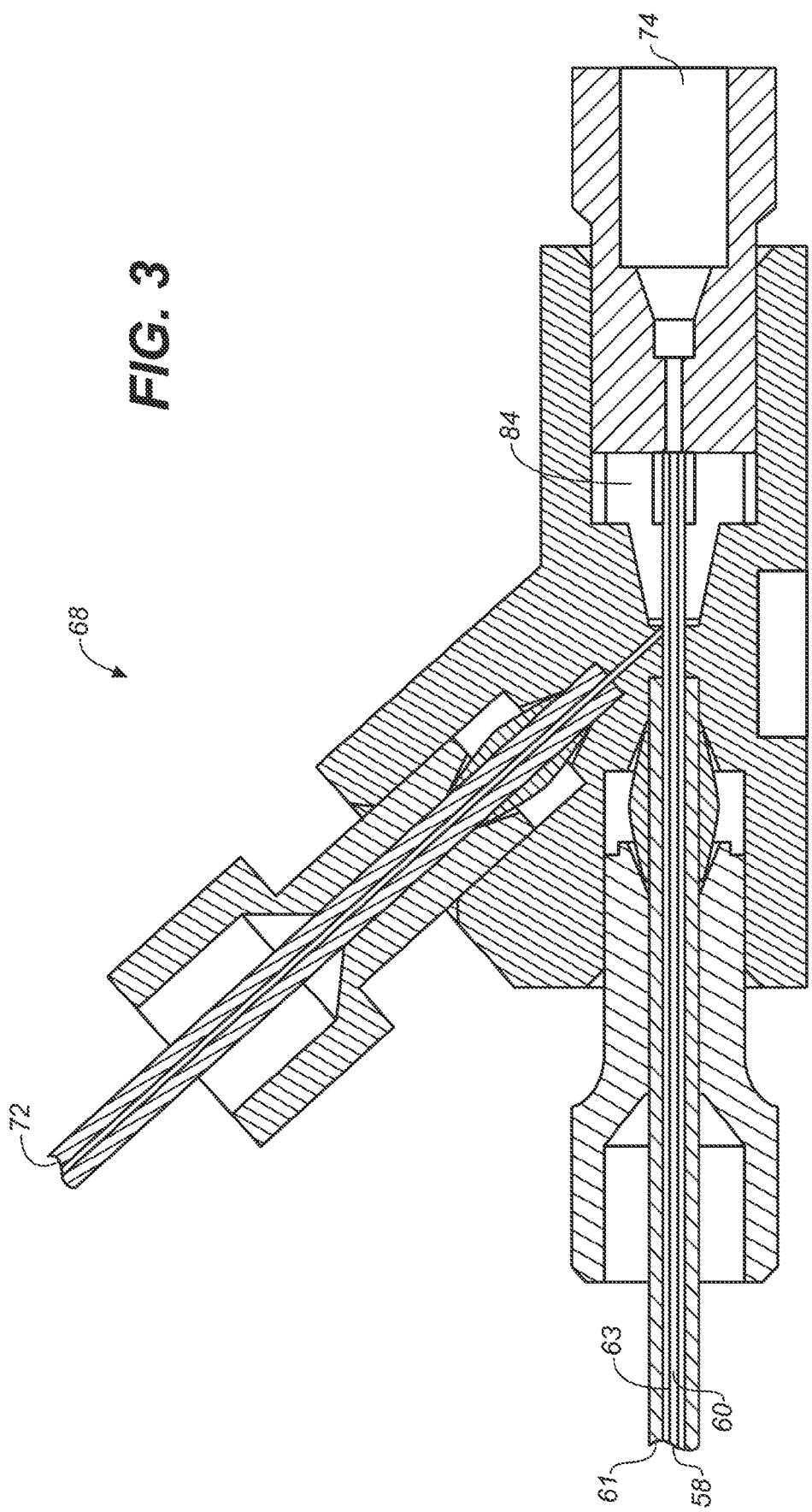
FIG. 3 is an enlarged view of the inlet end of the gas removal assembly of FIG. 2.
Figure 4:
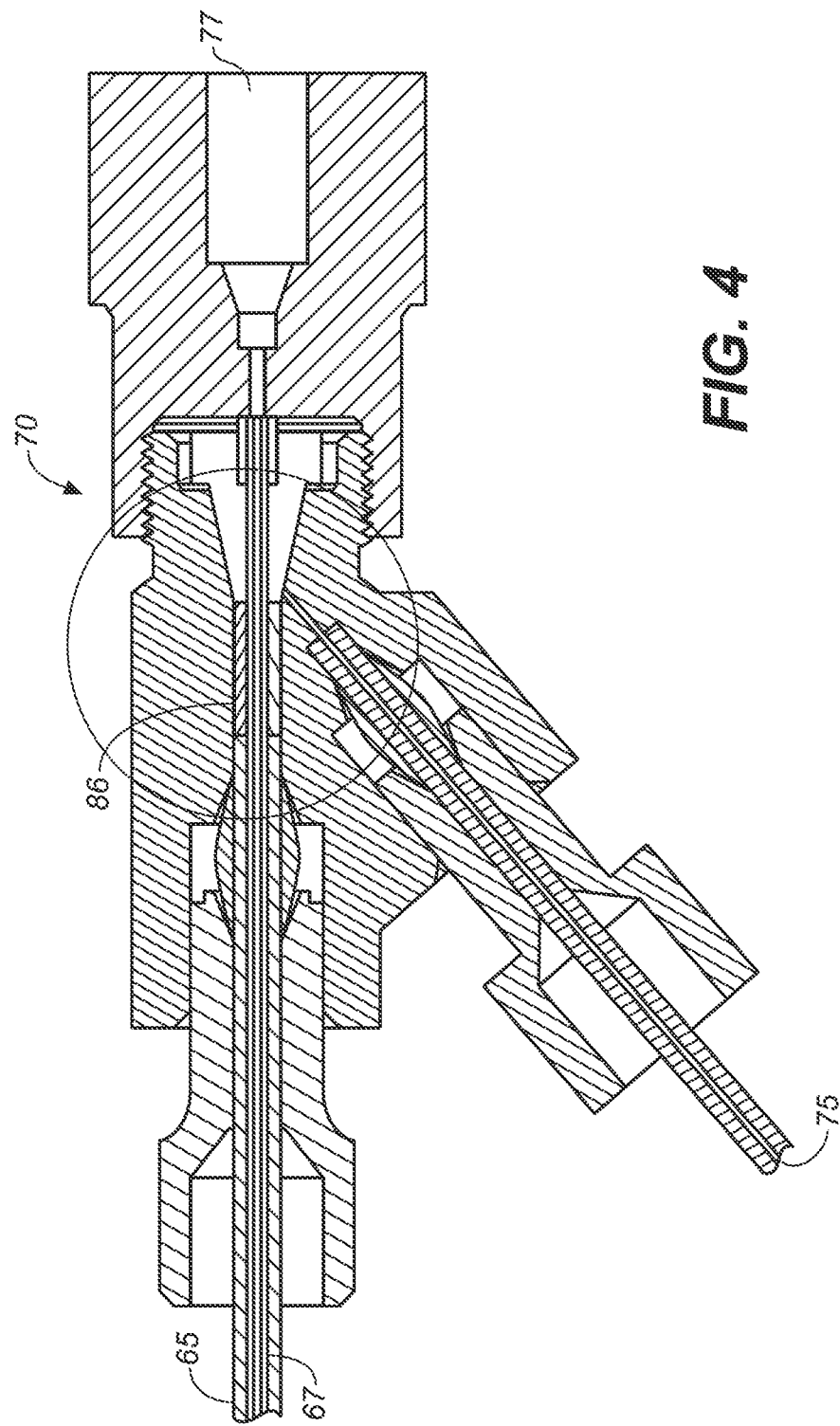
FIG. 4 is an enlarged view of the outlet end of the gas removal assembly of FIG. 2.

Turning now to FIGS. 2-4, the degas assembly and method of removing gas in accordance with the present invention will now be described in more detail.

Various aspects of the gas removal device are similar to the device described in U.S. Pat. No. 5,045,204 to Dasgupta et al., the entire contents of which are incorporated herein for all purposes by this reference.

Degas assembly 39 includes an inlet end 54 and outlet end 56 connected by fluid channels. In various embodiments, the degas assembly includes a low pressure fluid channel 58 for carrying a wash fluid 60 at a first pressure and a pressurized or high pressure channel 61 for carrying an eluent, or any gas-containing product, at a second pressure. The second pressure is higher than the first pressure.

"High pressure" and "low pressure" are to be understood as used in the analytical, chemical, and mechanical arts and are generally used with reference to each other under operational conditions.

"High pressure" generally refers to an elevated pressure. In various respects, "high pressure" refers to a pressure downstream from the pump and above the "low pressure" or local system pressure. In various respects, "high pressure" refers to a pressure above about 1000 psi, in some embodiments above about 3000 psi, in some embodiments above 3300 psi, in some embodiments between about 3300 psi and about 5000 psi, and in some embodiments above about 5000 psi.

In some respects, "high pressure" and "pressurized", "high pressure channel" and "pressurized channel", and "high pressure channel member" and "pressurized channel member" are used essentially interchangeably.

"Low pressure" refers to an unaltered local pressure or pressure below the "high pressure." In various respects, "low pressure" refers to a decreased pressure level obtained by a process or device of the invention.

"Wash fluid" refers generally to a fluid or other means for washing or evacuating the removed gas species from the channel. In various respects, "wash fluid" refers to a gas or void such as a vacuum. "Liquid" and "aqueous" are used essentially interchangeably. In various aspects, the wash fluid is essentially 100% organic solvents. In various aspects, the wash fluid is a mixture of water and organic solvents.

"Channel" is to be understood as generally used in the chemical and mechanical arts and generally refers to any of a variety of passageways for carrying a liquid or gas and includes, but is not limited to, grooves, conduits, and tubes. A "channel" may be in an open (e.g. groove) or closed (e.g. conduit) form.

A degas separator 63 is positioned between low pressure fluid channel 58 and pressurized fluid channel 61. The degas separator defines a fluid barrier between the low pressure fluid channel and pressurized fluid channel. The separator 63 is configured to retain liquid in the pressurized fluid channel while allowing gas to flow through the separator to the low pressure fluid channel.

In various embodiments, the pressurized fluid channel extends along an outer periphery of the low pressure fluid channel. "Periphery" is to be understood as used in the art and refers to the perimeter, outer surface, or exterior of the respective structure. The pressurized channel may extend along a portion or all of the outer periphery in the circumferential (transverse) or longitudinal (lengthwise) directions.

In various embodiments, pressurized channel member 65 and low pressure channel member 67 are tubes. In various embodiments, the low pressure channel member is an inner lumen formed within the outer pressurized channel member such that the pressurized channel member envelopes or surrounds, in whole or in part, the low pressure channel member. In various embodiments, the central lumen forms the low pressure fluid channel, an annular space between the central lumen and the outer tubing defines the pressurized channel, and the degas separator is the wall of the central lumen.

Pressurized channel 61 is defined by a higher pressure channel member 65, and low pressure channel 58 is defined by a low pressure channel member 67. The second pressure in pressurized channel 61 is higher pressure than the first pressure in low pressure channel 58.

The exemplary gas separator is a diffusion membrane that allows gas to permeate therethrough but retains liquid on one side. In various embodiments, the degas separator blocks substantial bulk liquid flow but allows gas to permeate. In other words, the membrane functions to permit the ready transmembrane passage of gas in the product flow while substantially preventing the transmembrane passage of liquid. The gas of interest generally permeates the gas separator in a conventional manner.

In the exemplary degas assembly, the wall of the low pressure fluid channel member is the degas separator (e.g. membrane). Accordingly, the material of the low pressure channel member affects the function of the degas assembly.

In various embodiments, the low pressure channel member 67 is formed of a chemically inert material such as an inert polymer. In various embodiments, the inner surfaces of the annular space between the pressurized channel member and low pressure channel member are chemically inert. The exemplary inner low pressure channel member is a PTFE tube. Suitable materials for the degas separator and/or low pressure channel member include, but are not limited to, polymers including polymethylpentene and polypropylene, and fluoropolymers such as polytetrafluoroethylene (PTFE), ethylene tetrafluoroethylene (ETFE), expanded-PTFE (ePTFE), perfluoroalkoxy (PFA), and fluorinated ethylene propylene (FEP). In various embodiments, the degas separator is formed of a material that is permeable by a gas under high pressure. In various embodiments, the degas separator is a gas-permeable polymer. In various embodiments, the degas separator is an amorphous fluoropolymer tube. The exemplary degas separator is a gas-permeable tube fabricated from Teflon® AF2400 amorphous polymer sold by DuPont. One will also appreciate that the low pressure channel member and/or degas separator may be treated with an additive or modified, such as by conjugation with a molecule. In various embodiments, the degas separator is a coating of an amorphous fluoropolymer on the exterior surface of a porous substrate tube such as Celgard®.

In various aspects of the invention, the degas separator is formed of a material selected to have one of a high gas permeability, high compressibility, low thermal conductivity, high creep resistance, and a combination thereof. The degas separator can also be used in conjunction with other features to enhance or promote separation based on ionic, chemical, and electrostatic forces. In various embodiments, the degas separator includes ion exchange sites.

The level of purity desired may depend on the application. The amount of gas separation generally depends on the diffusion properties of the gas separator, time, pressure, and diffusion area. One of skill will understand from the description herein the manner for configuring the gas separator to remove the gas and obtain the desired purity of the resulting gas-free liquid product. For example, the separation process may be configured as a multi-step process using a plurality of separation devices or by feeding product from outlet back into the degas assembly for further separation. In various embodiments, the degas assembly separates between about 50% and about 100% of the gas that enters the inlet end. In various embodiments, the degas assembly separates at least about 50% of the gas that enters the inlet end. In various embodiments, the degas assembly separates at least about 60% of the gas that enters the inlet end. In various embodiments, the degas assembly separates at least about 70% of the gas that enters the inlet end. In various embodiments, the degas assembly separates at least about 80% of the gas that enters the inlet end. In various embodiments, the degas assembly separates at least about 90% of the gas that enters the inlet end.

In various embodiments, the pressurized channel member 65 is formed of a chemically inert material, preferably an inert polymer. The exemplary pressurized channel member is a reinforced polyetheretherketone (PEEK) tube.

Suitable materials for the pressurized channel member include, but are not limited to, polymers such as fluoropolymers, stainless steel, and elastomers. In various embodiments, the pressurized channel member is formed of a high tensile polymeric material such as PEEK. One will appreciate, however, that the selection of materials and configuration will likely depend on the application and materials to be separated.

The exemplary degas assembly includes an inlet housing 68 and outlet housing 70. In the exemplary assembly, polymeric interface tees are attached to each end of the assembly to achieve fluid sealing of the high pressure channel. The two interface tees function to direct the stream of KOH solution containing hydrogen gas from the eluent generator into the exemplary high pressure channel between the outer tubing wall of the inner low pressure tubing and the inner wall of the high pressure outer tubing.

The inlet housing includes an eluent inlet 72 for connecting to eluent generator 35 and a wash inlet 74 for connecting to a wash source. In the exemplary system, recycled fluid serves as the wash fluid and detector 47 serves as the wash source. Outlet housing 70 includes an eluent outlet 75 and a wash outlet 77.

Low pressure fluid channel 58 is fluidically connected to wash inlet 74 at one end and wash outlet 77 at an opposite end. Pressurized fluid channel 61 is fluidically connected to eluent inlet 72 at one end and eluent outlet 75 at an opposite end. Thus, the pressurized eluent flow is directed through the pressurized channel and the low pressure wash that flushes to waste is in the low pressure channel. Eluent from the outlet housing flows to column 44. The wash fluid and the eluent flow may flow concurrently or in opposite directions.

As used herein, "end" is to be understood broadly and refers to a region, portion, or side adjacent the end point. "Opposite end" generally refers to a different region or portion on an opposite side. In various respects, "end" and "opposite end" refer to points upstream and downstream from each other as would be understood by one of skill in the art from the description herein.

In exemplary degas assembly 39, low pressure fluid channel 58 and pressurized fluid channel 61 are substantially coaxial tubes. The low pressure fluid channel member is a tube centrally located in the outer pressurized channel member. The exemplary pressurized channel member serves as a sheath or protective jacket for the fluid flow therethrough and may include a protective outer covering. As will be appreciated from the description herein, the exemplary degas assembly thus is configured for a low pressure, flow-through low pressure inner channel member and a higher pressure, flow-through space between the inner low pressure channel member and outer high pressure channel member.

The exemplary high pressure channel member has sufficient wall thickness to withstand a wide range of pressure. In various embodiments, the wall thickness is sufficient to withstand pressure between 0 psi and about 5000 psi or higher. The gas-containing eluent stream is exposed to the outer surface of the low pressure channel tubing under pressure.

In view of the pressure differential between the high and low pressure channels, a compressive force is exerted on the inner, low pressure channel member. The degas assembly is able to withstand high pressure in the pressurized channel for multiple reasons. First, the degas separator (e.g. the wall of the inner lumen) defining the low pressure channel is placed in compression. Many materials of interest, such as amorphous fluoropolymers, exhibit greater strength in compression than tension. Accordingly, much higher pressures can be applied before the material fails. Second, in the exemplary assembly, the inward pressure exerted by the high pressure flow on the inner channel member is counterbalanced by an opposing pressure inside the inner low pressure channel. In the exemplary assembly which includes coaxial flexible tubes, the fluid in the low pressure channel is compressed and provides a countervailing force. In various embodiments, the wash fluid is selected, or the wash fluid channel is pressurized, to achieve a desired pressure in the wash fluid channel thereby increasing the maximum pressure achievable in the high pressure channel.

The method of making the degas assembly in accordance with the present invention will now be described. The low and pressurized channel members are formed by conventional techniques such as extrusion. The channel members may be standard polymeric tubing supplied by a vendor. The channel flow portion of the degas assembly is formed by threading the low pressure tube through the pressurized tube. In the exemplary assembly, the channel members are loose and not fastened to each other except in the inlet and outlet housings as described.

Figure 5:
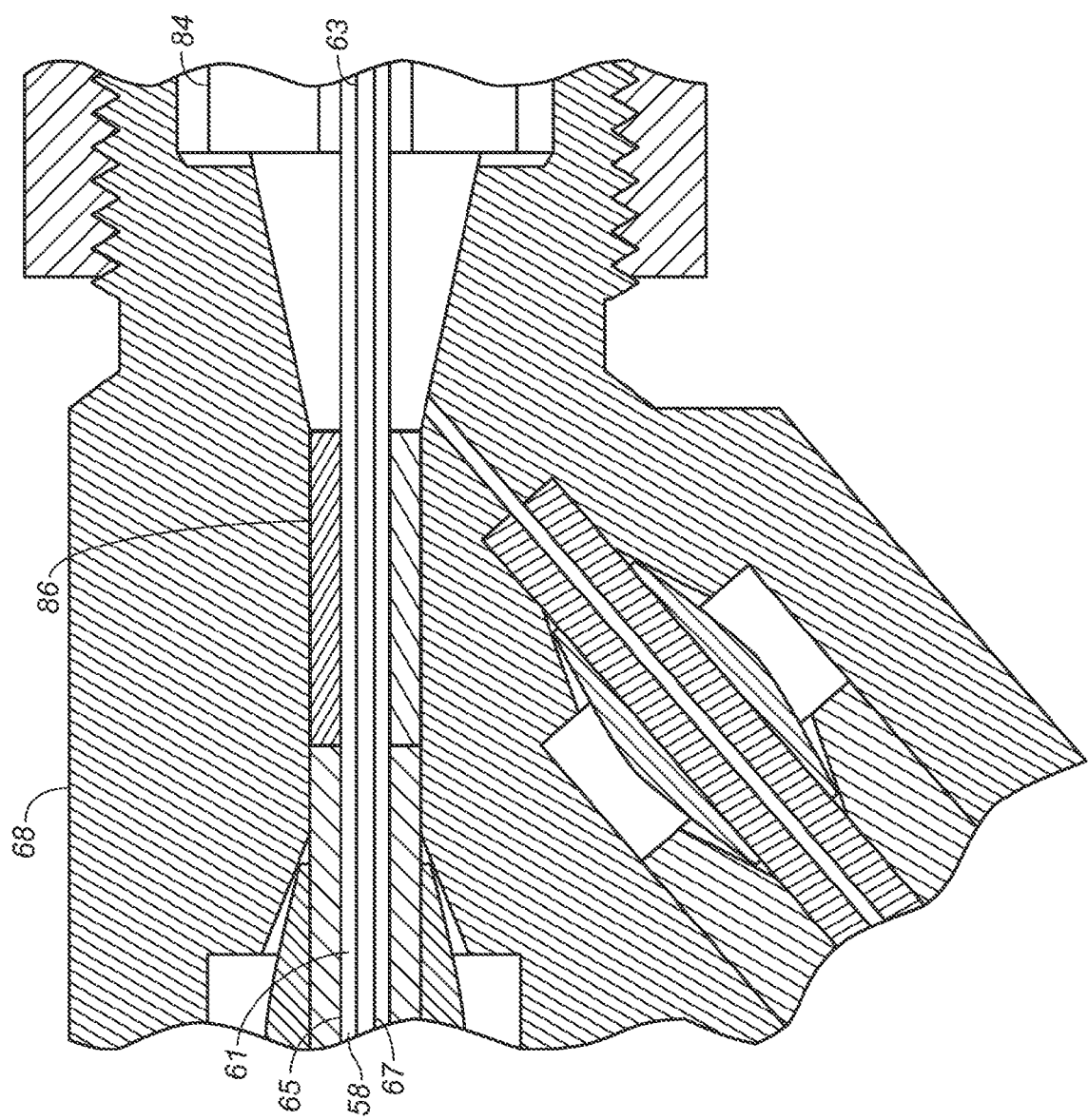
FIG. 5 is an enlarged view of a portion of the degas assembly inlet of FIG. 4.

Referring to FIGS. 4-5, exemplary housings 68 and 70 are configured as interface tees to attach to each end of the channel members and form a tight seal to ensure gas and liquid do not leak. The housings include inlets and outlets to port the flow path as described herein.

The pressurized channel member and low pressure channel members are fastened in place by attachment at each end to the inlet and outlet housings using ferrules 79. The ferrules clamp down on the channel member ends to secure them in place. In the exemplary system, the channel members are made of flexible polymer that deforms in response to the clamping force of the ferrules.

Figure 6:
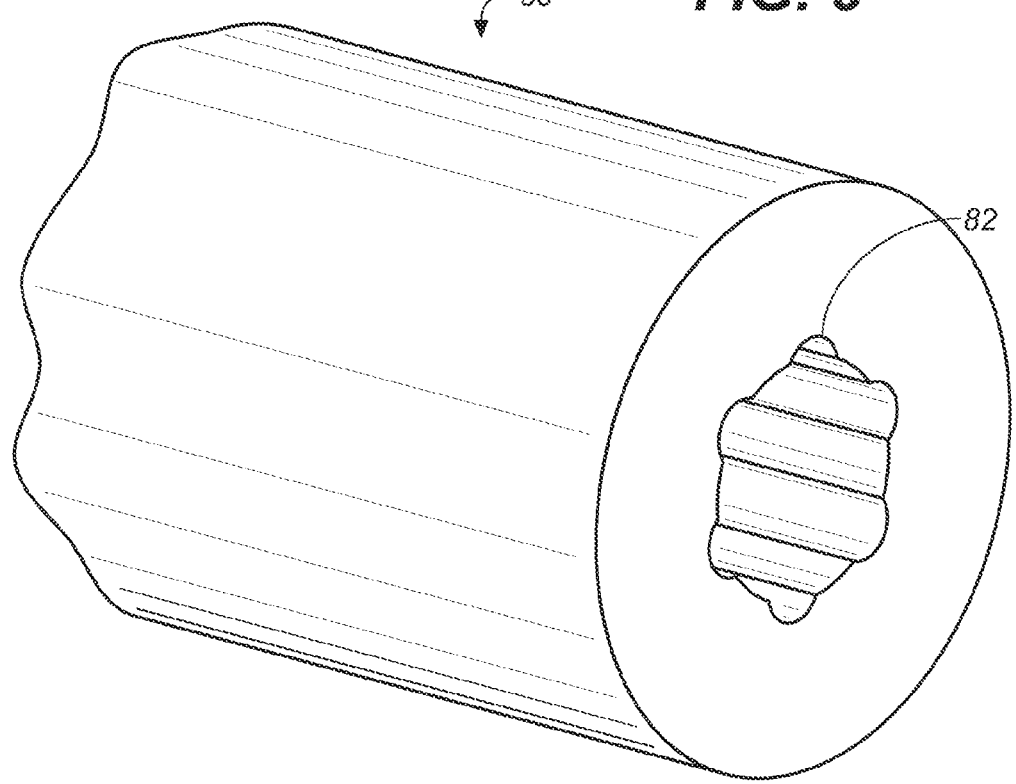
FIG. 6 is an enlarged perspective view of an end of the outer protective jacket of the assembly of FIG. 2, illustrating a splined pattern on an inner surface.
Figure 7:
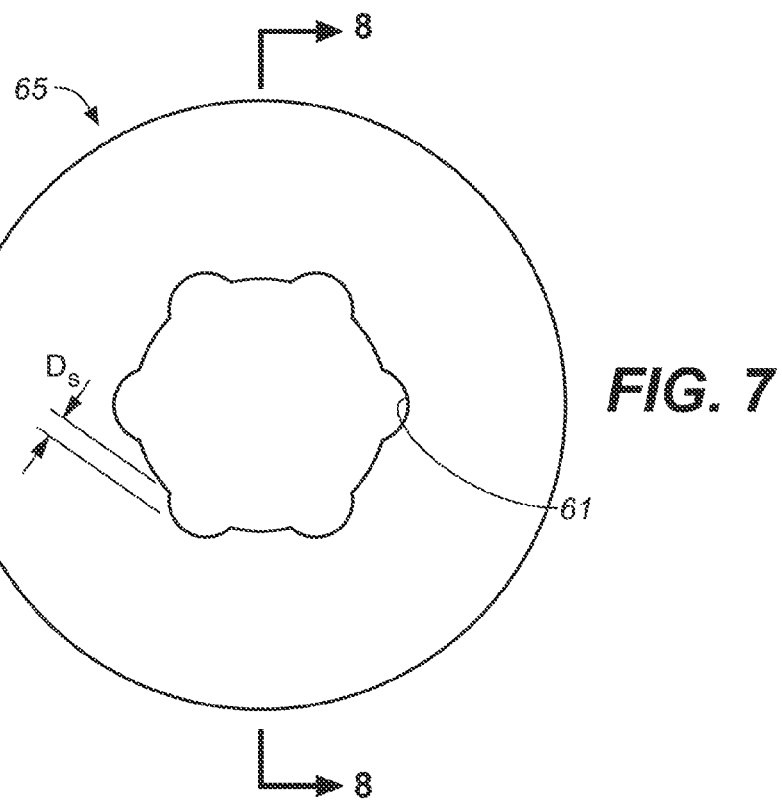
FIG. 7 is a front view of the end of the outer protective jacket.
Figure 8:
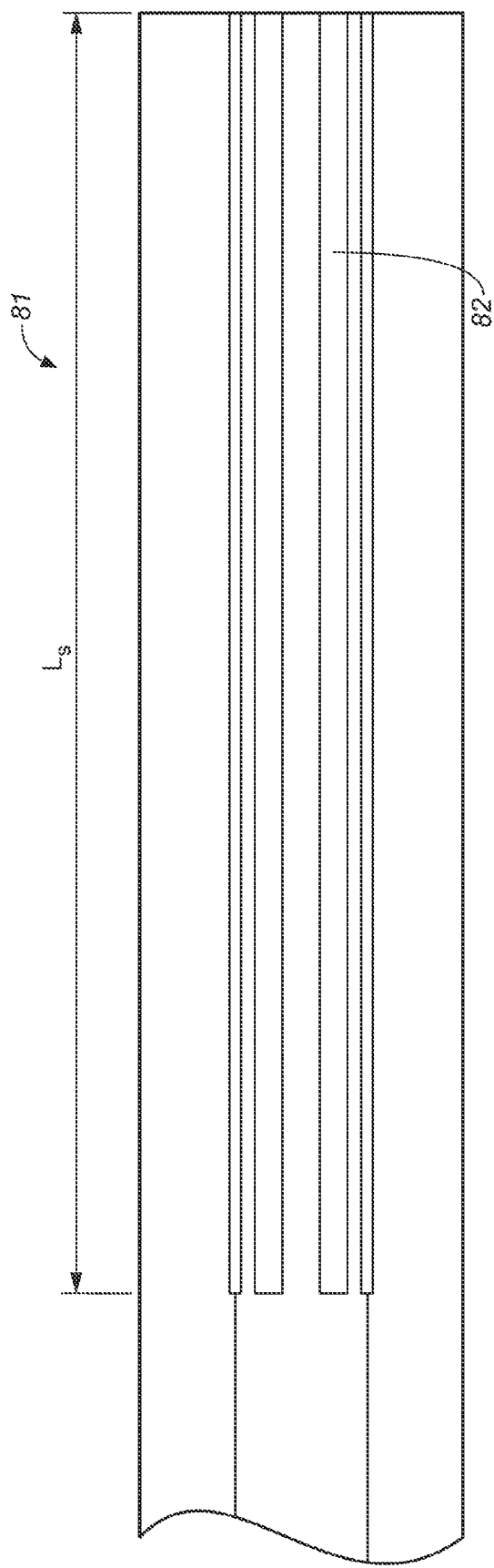
FIG. 8 is a cross-sectional view taken through the line 8-8 of FIG. 7.

As shown in FIGS. 6-8, exemplary degas assembly 39 includes a pressurized channel member (outer tubing) with a splined portion 81 including splines 82 (shown in FIG. 6). The splines are relatively rigid such that they are not crushed when the end of the high and low pressure channel members are clamped to the outlet housing as shown in FIG. 4. Instead, the splined portion essentially maintains its shape so fluid can pass through the splines. The splined portion has a length of $L_S$, and the splines have a depth of $D_S$ (shown in FIGS. 7 and 8).

In various embodiments, the splined portion is positioned at one end of the channel member and extends inwardly from the end along a portion of channel member. The length of the spline feature may be at least about 0.01 inch, at least about 0.375 inch, or longer. The spline feature may extend from each end of the tubing. One will appreciate that the splined portion may also extend along essentially the entire length.

The spline feature allows the use of a ferrule fitting in each to seal the high pressure inside the high pressure tubing without sealing off the annular space between the outer surface of the gas permeable inner tubing and inner surface of the high pressure tubing where the KOH solution containing hydrogen gas flows.

Figure 10:
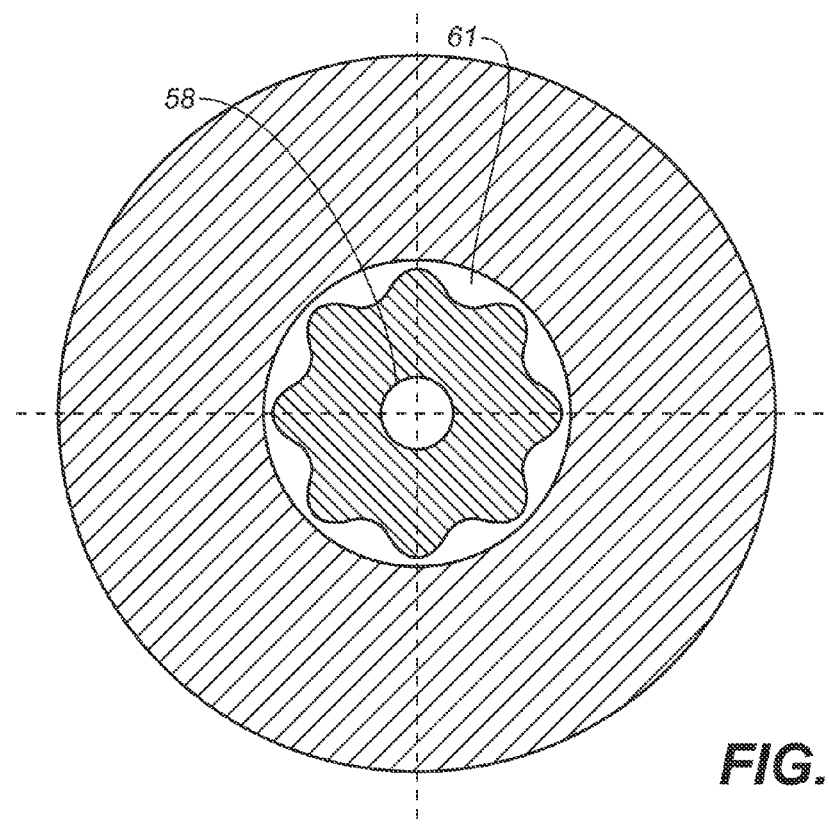
FIG. 10 is a cross-sectional view of tubing for a gas removal apparatus similar to that of FIG. 1, illustrating an inner channel member having a non-circular periphery.

The exemplary outer pressurized tubing has a non-circular starfish shape (best shown in FIG. 6). Alternatively, the inner low pressure tubing may have an irregular shape as shown in FIG. 10. The irregular fluting surface increases the diffusion surface area without requiring greater wall thickness. One will appreciate from the description herein that other shapes and configurations may be employed to increase efficiency and performance of the device accordingly. In various embodiments, the inner surface of the tubing has a shape selected from the group consisting of square, pentahedral, hexahedral, and octahedral. The exemplary non-circular shape allows the use of a ferrule fitting to seal the high pressure inside the tubing without sealing off the annular space between the outer surface of the gas permeable tubing and inner surface of the polymeric shield tubing where the KOH solution containing hydrogen gas flows.

The spline feature of the high pressure outer tubing may be prepared by using a heat stamping method with a heated spline-forming tool made of stainless steel. An extrusion tool may be used to produce the high pressure outer tubing with the spline feature, which extends along the entire length of the tube. Additionally, a special extrusion tool may be fabricated to produce the low pressure inner tubing with a spline feature similar to that shown in FIG. 10.

With reference back to FIGS. 3-5, the method of manufacturing the exemplary tubing of the degas assembly will now be described. The inlet ends of the low and pressurized channel members are attached to the inlet housing first using conventional techniques. The outlet ends are then attached using the following technique.

At outlet end 56 of the degas assembly, the exemplary tubing forming the low pressure channel member is threaded through the wash fluid outlet port in the housing. The outer pressurized tubing does not extend to the end of the inner low pressure tubing such that the inner tubing can be pulled through the port past the end of the housing. The end of the tube is pulled a sufficient distance past the housing to allow easy access to the end. With the end extending freely out of the back of the housing outlet, the end of the tubing is flared to provide a backstop. Next the tubing is pulled back towards the inlet end until the flared portion engages the fluid outlet port to form a fluid seal.

Figure 9:
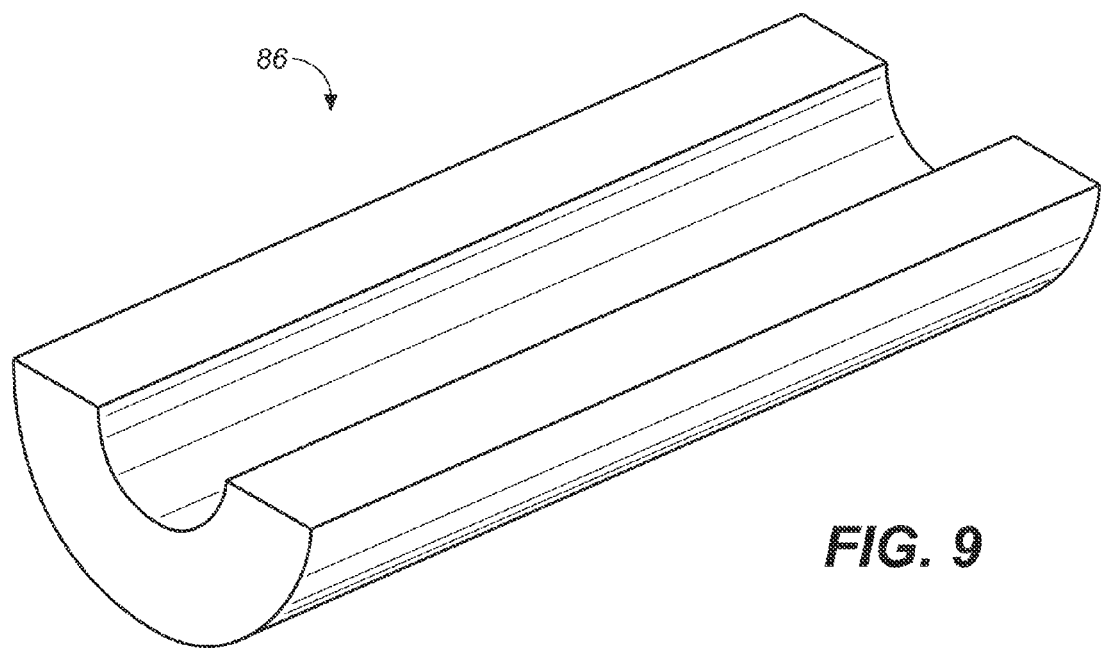
FIG. 9 is an exploded view of one of half of the makeup assembly of the gas removal assembly of FIG. 2.

As best seen in FIGS. 5 and 9, in the exemplary degas assembly, each end of the gas permeable inner flow channel member is thermally flared. The flared end tubing may be compressed against the polymeric fitting components of the interfacing housing so that the entire fluidic pathway can be leak-free and capable of withstanding high pressure.

A support ring 84 is optionally provided to fix the tubing in position and enhance the seal. The seal is sufficient to prevent leaking under high pressure. With the end of the low pressure tubing sealed to the housing, a gap is formed around the end of the tubing, which corresponds to the distance past which the tube extended during the flaring process.

The exemplary degas assembly includes a makeup assembly 86 for enveloping the low pressure tube and filling the gap left around the low pressure tube. In the exemplary embodiment, the makeup assembly is loosely placed around the low pressure channel member and pinched between support ring 84 on one end and pressurized channel member 65 on the opposite end. The makeup assembly resides in the gap to minimize dead space in the system. The exemplary makeup assembly is configured to provide a fluid conduit between pressurized channel member 65 and eluent outlet 75 of outlet housing 70.

The makeup assembly is configured as a two-piece clamshell (portion of makeup assembly best shown in FIG. 9). The two-piece design allows the makeup assembly to be easily attached to the end of the inner tube. The exemplary makeup assembly is about the same length or slightly shorter than the gap formed by the take-up of the inner tube after it is fastened by the flaring technique above. As described above, this gap corresponds to the slack in the tube when it is pulled through the housing.

In contrast to conventional devices and methods, the makeup assembly of the present invention provides for easier and faster assembly of the gas removal device of the present invention.

It is desirable to reduce voids and dead space in fluid systems, and chromatography systems in particular. Consequently, the makeup assembly beneficially reduces dead space that would otherwise result around the inner tube.

In various respects, the method of using the degas assembly and system in accordance with the present invention is similar to that described in U.S. Pat. No. 6,225,129, which is incorporated herein for all purposes by this reference.

With reference to FIGS. 1-2, in operation, high pressure eluent from eluent generator 35 flows to degas assembly 39 via the inner diameter (ID) of the system tubing and enters the first interface housing 68. As described above, the inlet and outlet housings have a low dead volume design. The inlet housing ports the eluent flow to the exemplary annular gap (i.e. pressurized channel 61) between the outer diameter of low pressure inner channel member 67 (in the exemplary case, Teflon® AF2400 tubing) and the inner diameter of pressurized channel member 65 (in the exemplary case, a PEEK tubing jacket). The pressurized channel member wall thickness is designed to withstand the high pressure of the eluent.

The eluent flow in the degas assembly is received from the eluent generator at high pressure. In various embodiments, the pressure is at least about 100 psi. In various embodiments, the pressure is at least about 3000 psi, and in some aspects at least about 3300 psi. In various embodiments, the pressure is at least about 5000 psi. The maximum pressure or peak pressure in some cases may be even higher.

With the high pressure eluent flow being on the outside of the inner gas-permeable tubing, the gas-permeable tubing material is in compression. In other words, the pressurized (high pressure) side is on the outside of the gas-permeable tubing instead of the inside. Thus, the burst pressure of the gas-permeable tubing is generally inconsequential. As the eluent flows in the annular gap corresponding to the pressurized channel, the gas is removed from the eluent solution and diffuses into the inner diameter of the low pressure channel member (e.g. the gas-permeable tubing).

With continued reference to FIGS. 1-2, the gas is removed from the gas-containing product by diffusion through the degas separator in a manner similar the degassing unit described in U.S. Pat. No. 7,390,386. The gassified eluent flows through the degas assembly where gas is separated from the liquid phase. As the gassified eluent flows through the gas-permeable tubing, gas diffuses through the member into the inner lumen and is removed by the flowing aqueous liquid stream. At the outlet end, the gas and liquid flow out of separate ports. Along the length of the pressurized channel, therefore, the amount of gas in the eluent solution decreases. In this way, the gas is separated and isolated by the degas assembly. As will be understood by one of skill in the art, the assembly can be dimensioned and configured to provide a desired amount of separation to achieve a desired sample solution purity.

The flowing aqueous liquid stream in the lumen also serves to prevent adsorption of carbon dioxide from the ambient air into the eluent stream. As described above, one source of the flowing aqueous liquid is the detector effluent. At the end of pressurized channel 61, the eluent flows into outlet housing 70, which mirrors the inlet housing, and is ported back to inner low pressure channel 58 of the system for directing to injector 42. After the sample has been injected into the separation column and thereafter detected at detector 47, the eluent (also referred to as regenerant) is directed back to the inlet housing 68 of the degas assembly. This time it is ported to the inner diameter of the low pressure channel member (e.g. 58) where the flow sweeps away gas that has diffused through the degas separator. One will appreciate from the foregoing that the exemplary system may generally be operated continuously. In the degas assembly, high pressure eluent may flow in the pressurized channel while recycled eluent flows through the low pressure channel.

One will appreciate from the description herein that the gas removal assembly may have other configurations in accordance with the present invention. For example, the assembly may be non-tubular.

Figure 11:
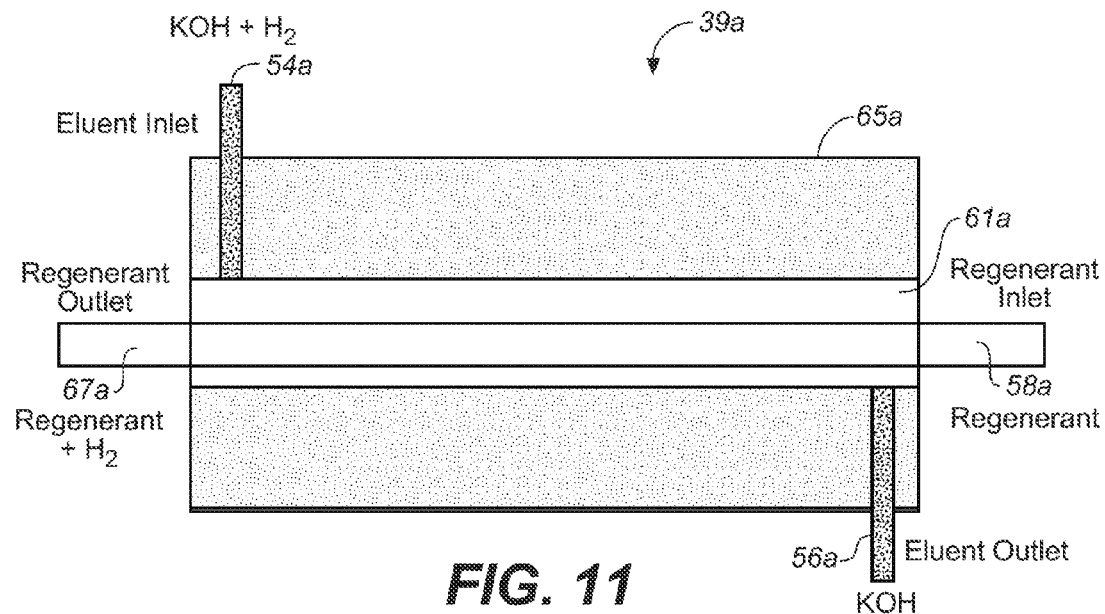
FIG. 11 is a schematic of tubing for a gas removal apparatus similar to that of FIG. 1, illustrating the low pressure flow and pressurized flow in opposite directions.

Turning to FIG. 11, a degas assembly 39a similar to degas assembly 39 is shown. Degas assembly 39a includes a gas permeable tubing positioned in a housing or jacket 65a. The housing may be made of high tensile strength polymer such as PEEK. The housing has an inlet port 54a and outlet port 56a to direct a stream of KOH solution containing hydrogen gas from the KOH eluent generator into the space between the outer surface of the gas permeable tubing and the inner surface of housing. Each end of the gas permeable tubing is thermally flared. The flared end tubing is compressed against the polymeric fitting components of the housing so that the entire fluidic pathway can be leak-free and capable of withstanding high pressure.

Figure 12:
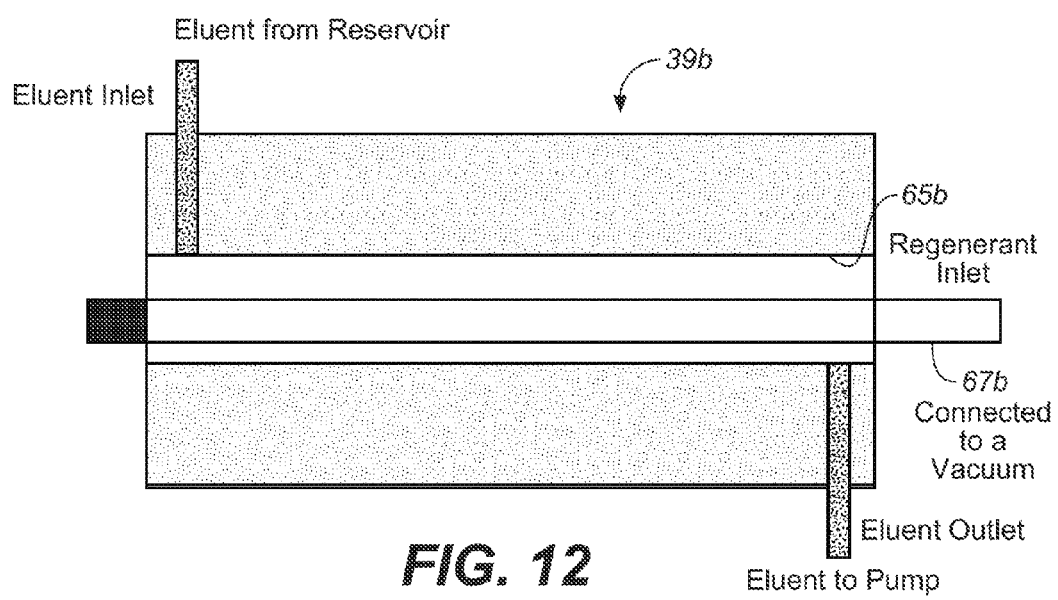
FIG. 12 is a schematic of tubing for a gas removal apparatus similar to that of FIG. 1, illustrating a vacuum line in place of a low pressure channel carrying an aqueous solution and a sleeve in accordance with the invention.

With reference to FIG. 12, a degas assembly 39b similar to degas assembly 39 and degas assembly 39a is shown. Degas assembly 39b is placed at the inlet of a fluid pump used in the ion chromatography or liquid chromatography system. The chromatography eluent to be degassed is directed through the space or channel between the outer surface of the gas permeable tubing 67b and the inner surface of housing 65b. One end of the gas permeable tubing is capped. The other end of the gas permeable tubing is connected to a vacuum. Under the applied vacuum, the gases in the eluent stream diffuse into the inner lumen of gas permeable tubing 67b and are removed.

Figure 13:
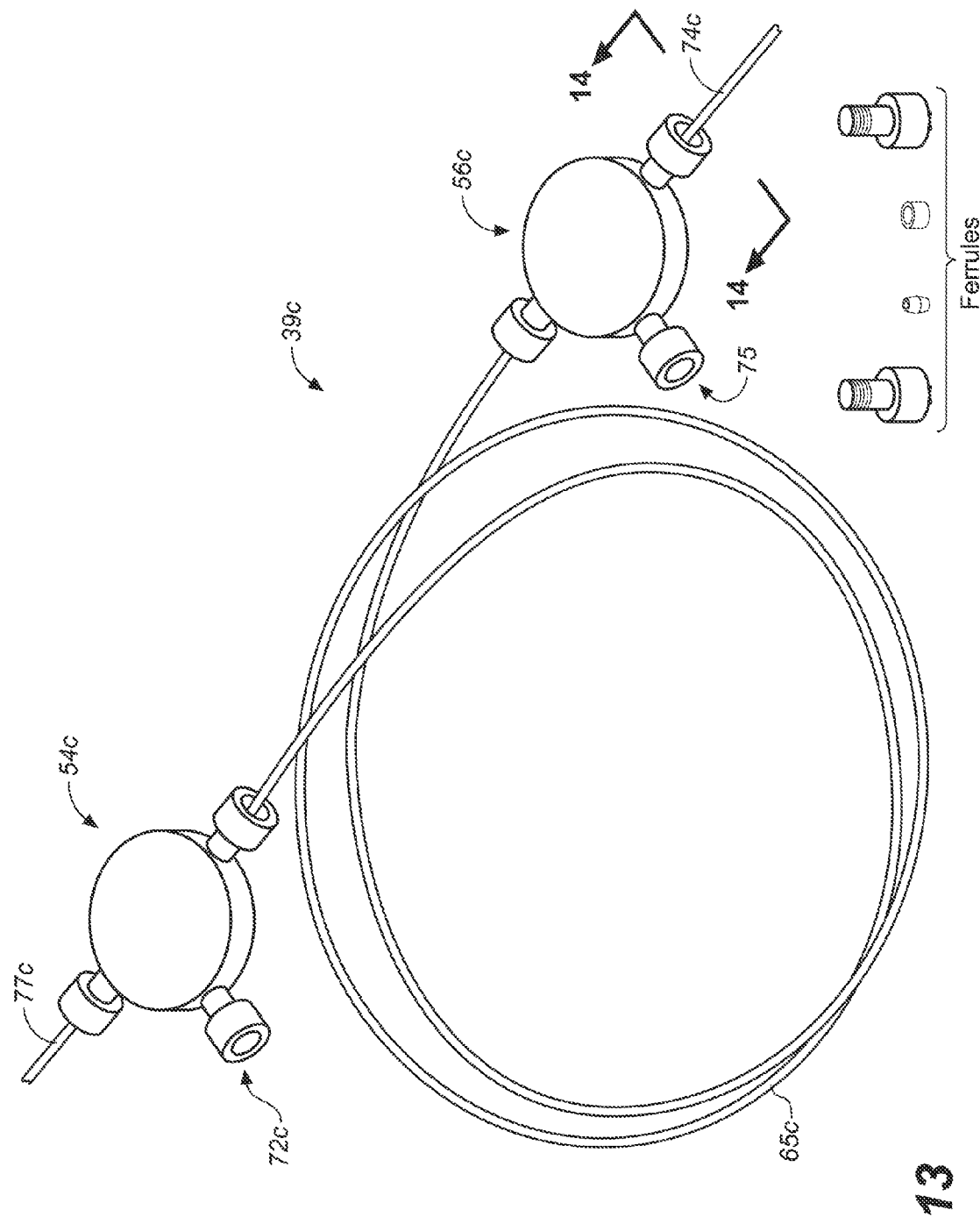
FIG. 13 is an assembly view of a gas removal apparatus similar to that of FIG. 1, illustrating alternative housings at each end for attachment to the eluent and wash fluid lines.
Figure 14:
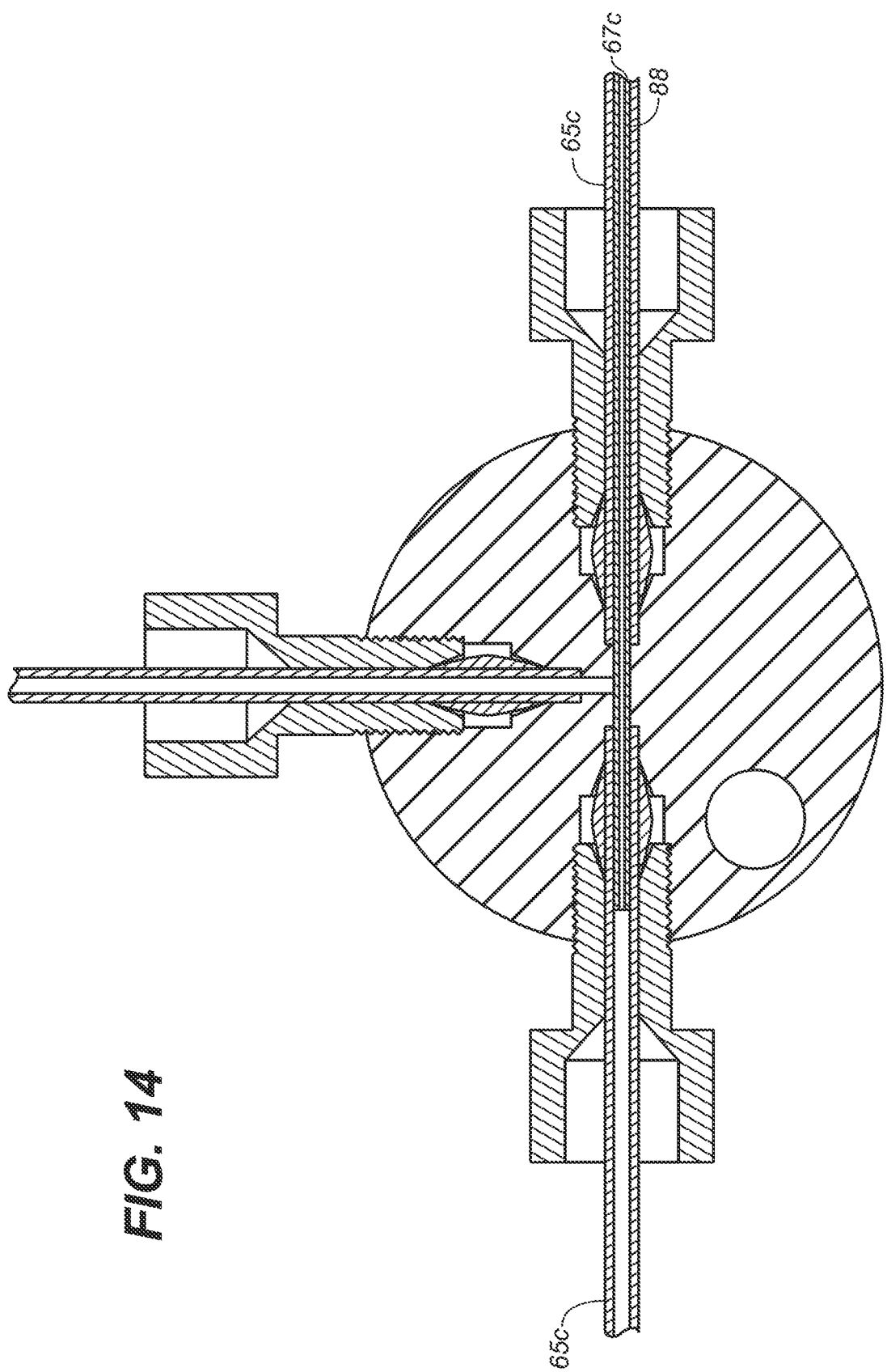
FIG. 14 is a cross-sectional view of one of the housings of FIG. 13 taken through the line 14-14.

Turning to FIGS. 13-14, a degas assembly 39c similar to degas assembly 39 is shown. Degas assembly 39c includes a piece of gas permeable tubing (e.g., 0.033-inch OD×0.008 ID AF2400 tubing) positioned inside a piece of polymeric shield tubing 65c capable of withstanding pressures up to 5000 psi or higher (e.g., 1/16-inch OD×0.034 ID PEEK tubing). Degas assembly 39c is configured and operates similarly to degas assembly 39 but includes two tees 54c, 56c in place of inlet and outlet housings 54, 56. The tees provide fluidic pathways to direct a stream of KOH solution containing hydrogen gas from the KOH eluent generator into the annular space between the outer surface of the gas permeable tubing 67c and the inner surface of housing 65c. In various embodiments, the polymeric shield tubing has an internal spline feature similar to that of degas assembly 39 (see FIGS. 6 and 10). In various embodiments, the entire length of polymeric shield tubing contains the spline feature. The gas permeable tubing at the degasser inlet end 54c and outlet end 56c is placed inside a short piece of polymeric tubing 88 which is used as a sleeve over the gas permeable tubing. The ID of the sleeve tubing is dimensioned to ensure that the gas permeable tubing is compressed against the inner lumen of the polymeric tubing by interference fit so the entire fluidic pathway is essentially leak-free and capable of withstanding high pressure. Inlet 54c and outlet 56c are configured similar to inlet 54 and outlet 56 except that ports are arranged in perpendicular fashion. The inlet and outlet housings are formed of a polymer.

The degas assembly and method of the invention has several advantages. As described above, the eluent can be degassed at a higher system pressure than conventional systems using electrolytic eluent generators. In particular, conventional degas assemblies use materials such as Teflon® AF2400 tubing with a theoretical burst pressure of about 3300 psi. In practice, the system can only achieve a maximum of about 3000 psi before failure. By contrast, the system in accordance with the present inventions can operate at a pressure approaching the maximum tensile strength of the material. With other configurations such as a reinforced outer jacket, the system pressure can be even higher. This allows use of the degas assembly in a greater variety of systems and configurations. For example, the degas assembly may be provided in-line on the high pressure side of the system after the pump. Conventional degas assemblies must be used off-line or in low pressure systems.

The high pressure capability of the degas assembly in accordance with the present invention also allows the system to be used for other applications such as RFIC-EG systems at elevated pressures. With the expanded range of system operating pressure, it is possible to increase the separation speed by performing separations at higher flow rates or using shorter separation columns packed with stationary phases of smaller particle sizes.

The exemplary annular degasser device offers improved degas efficiency. In the exemplary system, the gas-containing eluent stream is exposed to the outer surface of the polymeric gas permeable tubing (e.g., Teflon AF2400 tubing). The outer surface area of the degas tubing is significantly higher than the surface area of the inner lumen of the degas tubing. For example, the typical dimension of Teflon AF tubing used in the Dionex RFIC-EG (reagent-free IC, eluent generation) systems is 0.032-inch OD×0.008 inch ID. In this case, the outer surface area is approximately 4 times the inner surface area. Since the degasser efficiency depends on the surface area, the degas assembly provides significantly improved degas efficiency.

The gas permeable tubing in the exemplary degas assembly can withstand much higher pressures without bursting due to the fact that the pressurized eluent stream flows outside of the outer surface of the gas permeable tubing and the tubing is under compression from the outer surface inwards. For applications of given operating pressures, it is possible to use thinner-wall gas permeable tubing to further improve the degas efficiency. The use of thinner-wall version of the costly gas permeable tubing (e.g., Teflon AF2400 tubing) reduces the degasser cost.

The annular degasser devices of the present invention can be constructed to have lower degasser volume since the degas assembly offers improved degas efficiency. To achieve the required degassing capability, degassers of lower dead volume can be prepared using the degas assembly of the present invention and the degas assembly may utilize shorter length degas tubing. The use of reduced length of the costly gas permeable tubing reduces the degasser cost. For example, Teflon AF2400 tubing currently costs about $50 per foot. The lower volume provides shorter gradient delay, improved gradient fidelity, and improved overall system performance in ion chromatography systems using electrolytic eluent generators. The degas assembly of the present invention can achieve significantly higher gradient fidelity. The improved efficiency and performance of the degas assembly in accordance with the invention also allows for use of separation columns with smaller particle sizes.

The degas assembly of the present invention makes it possible to operate an ion chromatography system using an electrolytic eluent generator at lower system operating pressures. To remove the gases from a gas-containing eluent stream using conventional degassers such as those in the Liu patent, it is necessary to add some backpressure after the degasser to "squeeze out" the gases from the eluent stream. It is often necessary to maintain a backpressure threshold of about 2000 psi to achieve the desired degas efficiency. In a typical ion chromatography system using the electrolytic eluent generator, a piece of PEEK tubing with smaller ID (e.g., 0.003-inch) of appropriate length is often used to add the pressure in addition to that generated by the separation column. This approach adds to the system operation complexity. Since the degas assembly of the present invention has improved degassing efficiency, it is possible to reduce the pressure threshold to lower pressures. The need to add an additional backpressure device may be eliminated entirely. The system reliability may also be consequently improved.

The degas assembly of the invention also allows the use of a greater number and variety of lower-pressure-rating, gas-permeable tubing materials at considerable cost savings. Some of these lower tensile strength materials also offer better gas permeability. The degas assembly may also provide better rejection of contaminants coming from the suppressor such as hydrogen peroxide and ozone.

EXAMPLES

The invention is further illustrated by the Examples that follow. The Examples are not intended to define or limit the scope of the invention.

Example 1

Use of Degas Assembly in an Ion Chromatography System Containing an IC Cube for Separation of Common Anions on a Capillary Anion Exchange Separation Column An ICS-5000 ion chromatography system (Dionex Corporation, Sunnyvale, Calif.) was used. The system consisted of a pump module, electrolytic eluent generator (EG) module, and a conventional-scale chromatography compartment (DC) module. A Dionex Chromeleon 6.8 chromatography data system was used for instrument control, data collection, and processing. The system was configured according to FIG. 1. A Dionex IC (ion chromatography) cube was used. The IC cube contained capillary-scale system components such as a degasser assembly, a sample injector, a separation column, an electrolytic suppressor, a carbonate removal device (CRD).

The degas assembly was constructed according to FIG. 2. The IC cube was physically placed in the upper compartment of the ICS-5000 DC module. The detection of analytes was accomplished using an ICS-5000 capillary conductivity detector. A capillary-scale electrolytic KOH eluent generator and a capillary CR-ATC was installed in the ICS-5000 EG module and controlled by the ICS-5000 EG module.

The exemplary degas assembly was formed using a PEEK tube for the outer pressurized channel member. The PEEK tube had a 2 mm outer diameter (OD) and 0.034" inner diameter (ID). The degas assembly had an outer diameter (OD) corresponding to the outer surface of the PEEK tube.

The inner channel member was AF2400 tube having an ID of 0.008" and OD of 0.033". The inner AF tubing was placed inside the PEEK tubing jacket. Two housings were attached to each end of the tubes to seal both ends and port flow in the correct flow path.

A flare seal design was used to seal the AF tubing against leaking from high pressure flow. The pressurized tube included a splined portion with LS=⅜" on each end. The internal splines had a depth, DS, equal to 0.375". The splines were found to allow a tight seal of the pressurized tubing under high pressure with a conventional ferrule fitting and without occluding the annular space for the eluent between the inner Teflon® AF2400 tube and outer PEEK tube.

A makeup assembly was provided around the AF tubing and between the end of the PEEK jacket and housing wall. The makeup assembly had a 2 mm OD, 0.034" ID, and length of 0.200".

Figure 15:
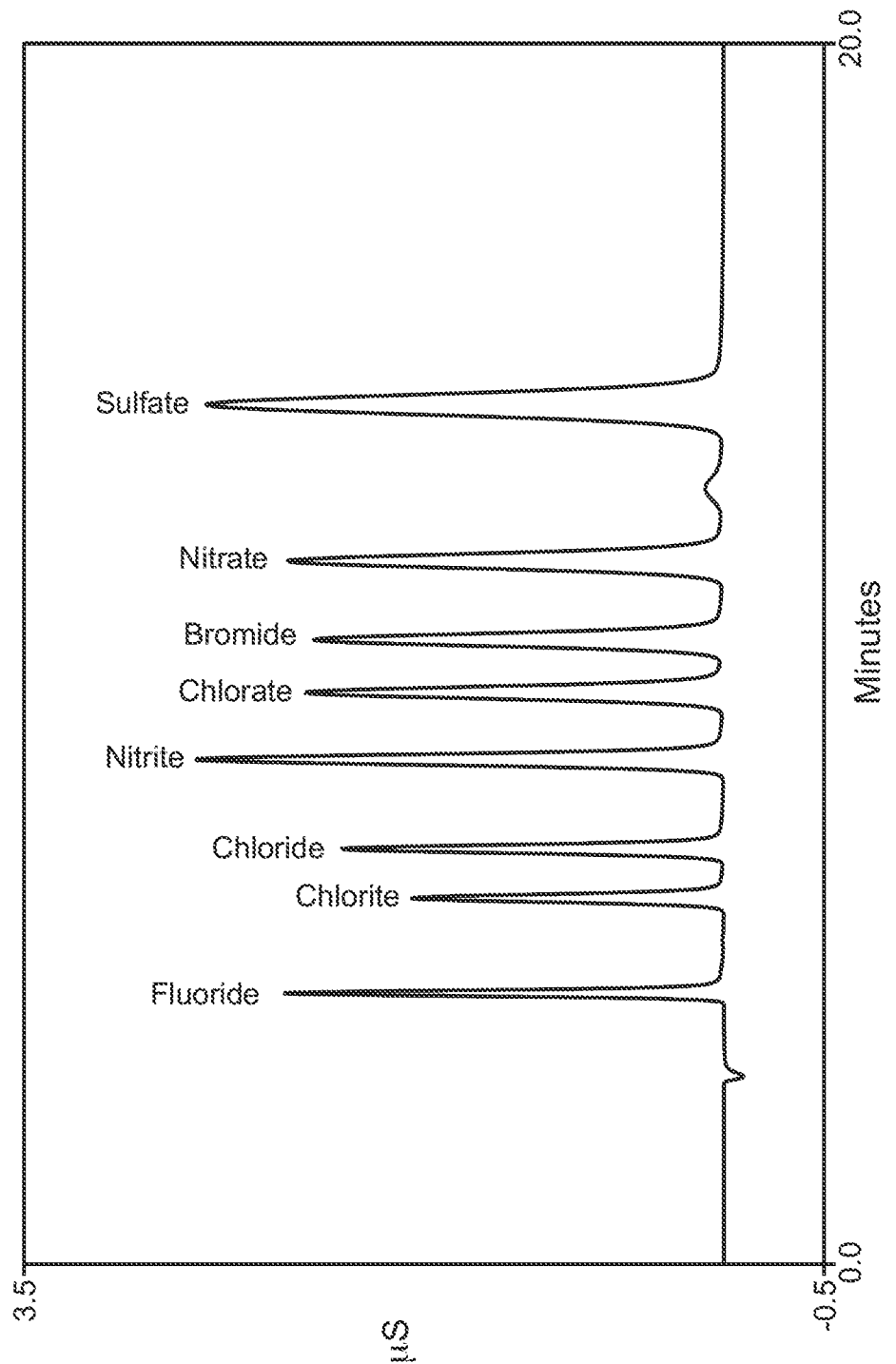
FIG. 15 illustrates the results of separation of eight common anions using the system of FIG. 1.

A capillary separation column (0.4 mm×250 mm) was packed with the Dionex AS19 anion exchange resin. FIG. 15 shows the separation of 8 common anions including fluoride, chlorite, chloride, nitrite, chlorate, bromide, nitrate, and sulfate obtained using the system under the eluting condition of 20 mM KOH at 10 μL/min. In FIG. 15, the y-axis is microsiemens and the x-axis is minutes. FIG. 15 shows an overlay of 30 consecutive separations of the target analytes. The results show highly reproducible separation of the target anions with analyte retention percent relative standard deviation (RDS) ranging from 0.047% for nitrite to 0.078% for sulfate, and analyte peak area percent RSD ranging from 0.28% for fluoride to 0.33% for bromate. These results demonstrate that the capillary ion chromatography system fitted with degas assembly of the invention can be used to provide reliable capillary-scale ion chromatographic separation of target anionic analytes using only deionized water as the carrier stream.

Example 2

Figure 16:
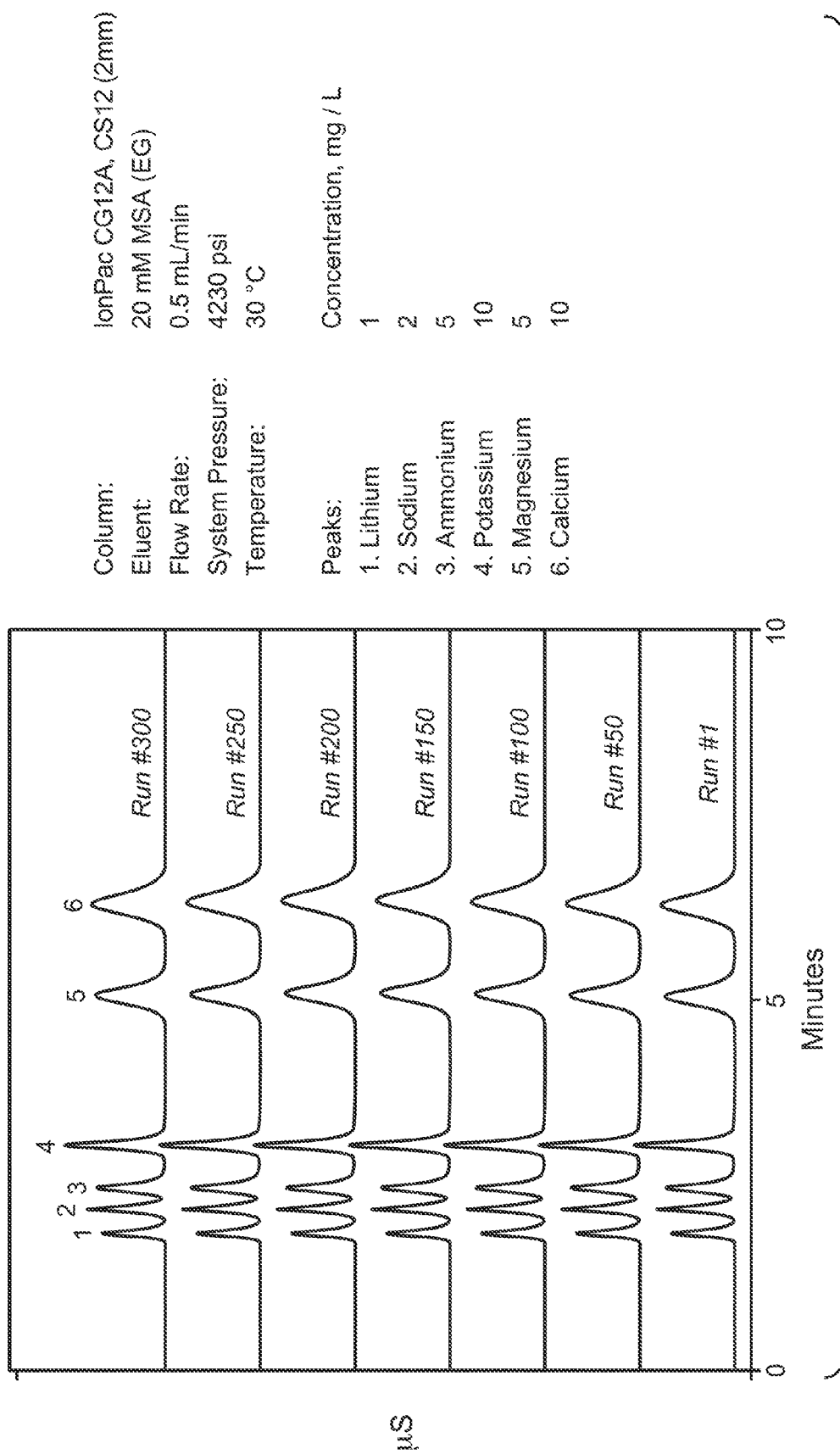
FIG. 16 illustrates the results of separation of six common cations using the system of FIG. 1 with the carbonate removal device removed.

Use of Degas Assembly in an Ion Chromatography System Employing an Electrolytic Methanesulfonic Acid Generator for Separation of Common Cations on a Cation Exchange Separation Column An ICS-2000 ion chromatography system (Dionex Corporation, Sunnyvale, Calif.) was used. The system was configured according to FIG. 1 except that the carbonate removal device was not used. A Dionex Chromeleon 6.8 chromatography data system was used for instrument control, data collection, and processing. The degas assembly was constructed according to FIGS. 13-14. Dionex CS12A and CG12 cation exchange columns were used. The separation was performed using 20 mM methanesulfonic acid at 0.5 mL/min. FIG. 16 shows the separation of six common cations. The results show highly reproducible separation of the target cations over three hundred injections. These results demonstrate that the ion chromatography system fitted with degas assembly of the invention can be used to provide reliable ion chromatographic separation of target cationic analytes using only deionized water as the carrier streams in conjunction with electrolytic eluent generator.

Example 3

Generation of KOH Eluent Using an EGC KOH Cartridge and a Degas Assembly

Figure 17A:
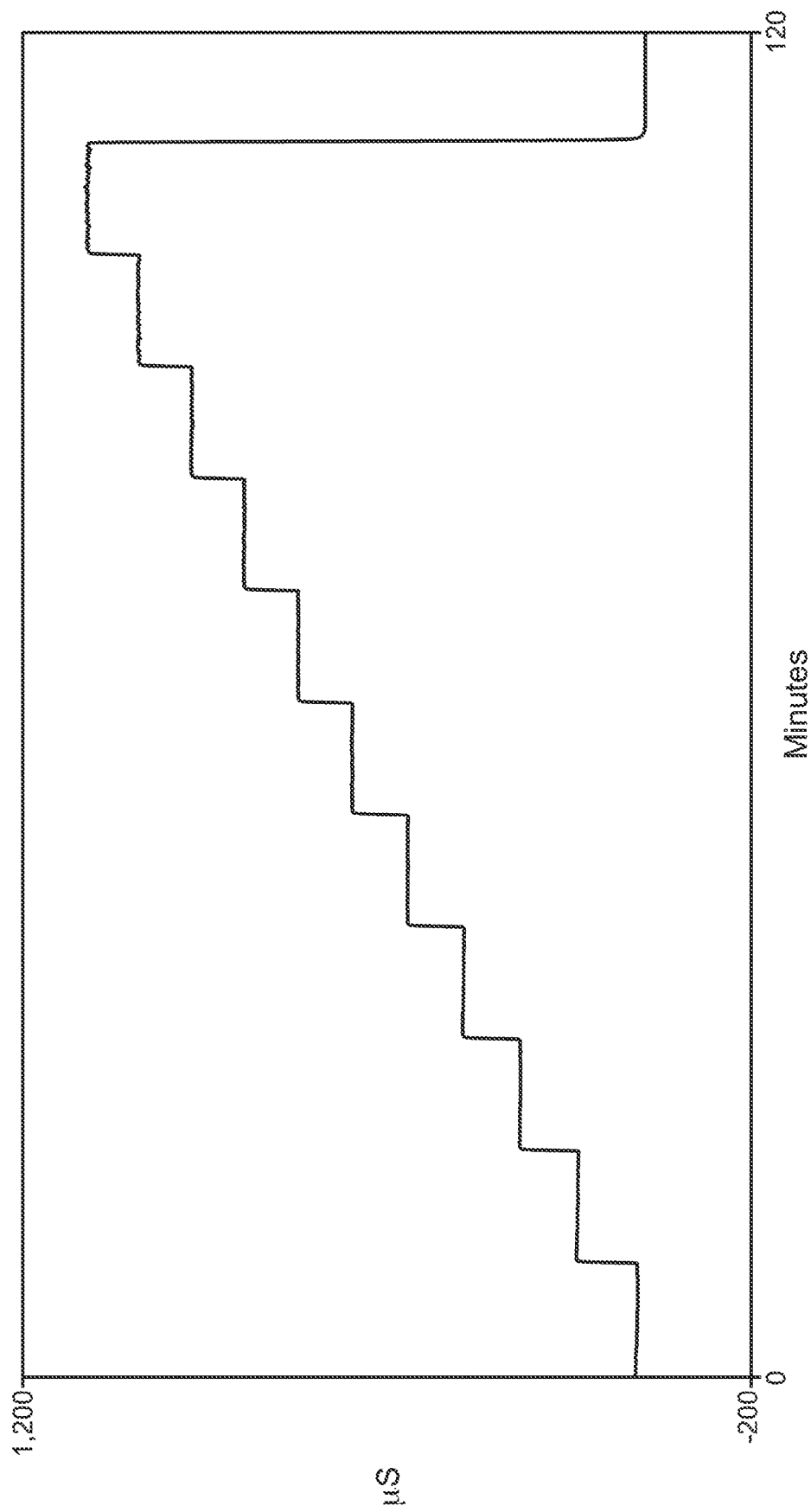
FIG. 17A shows the conductance of KOH eluents using the system of FIG. 1 with a conventional gas removal device.
Figure 17B:
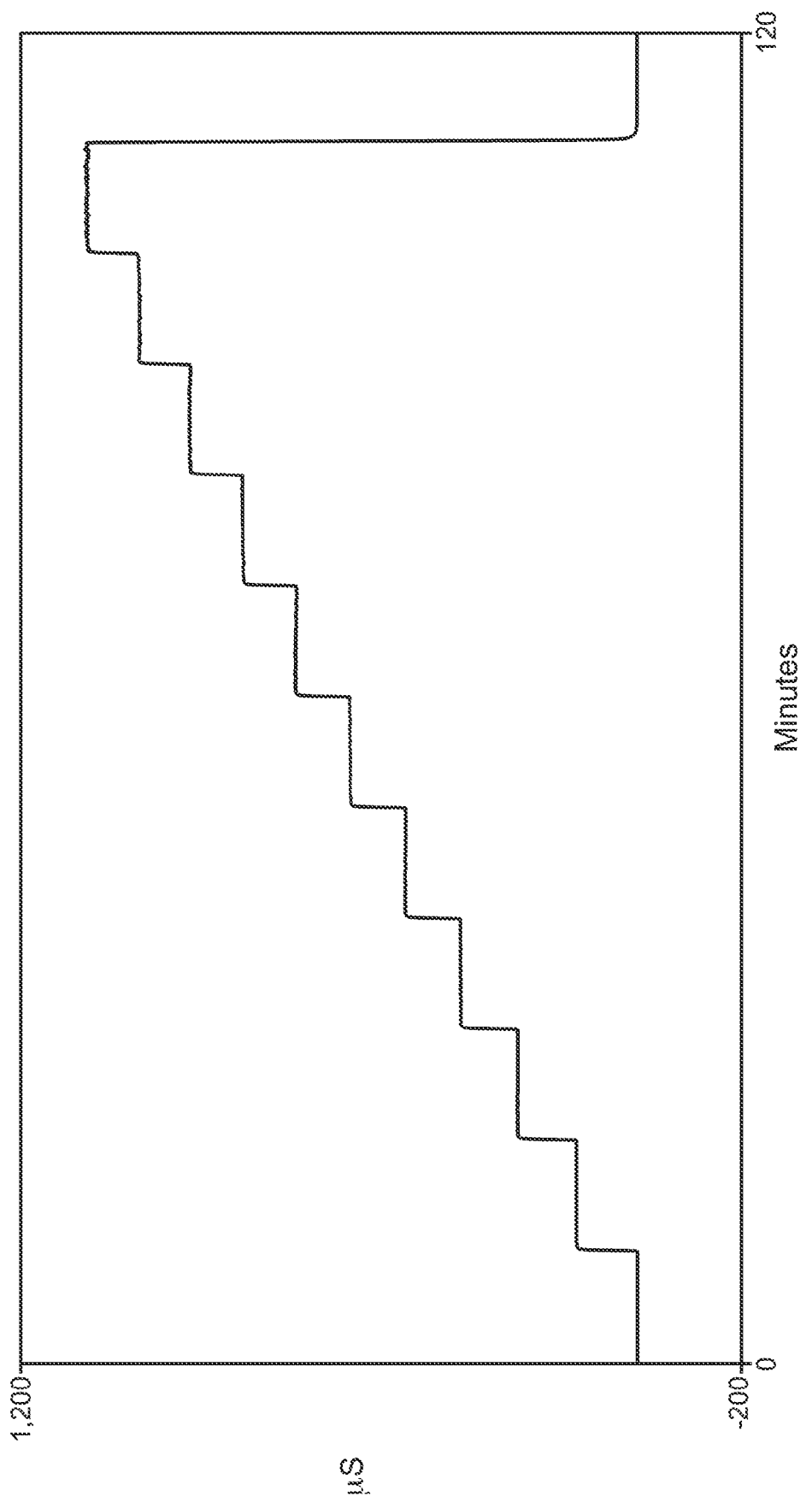
FIG. 17B shows the conductance of KOH eluents using the system of FIG. 1 with a gas removal device in accordance with the present invention. The gas removal flowpath of the system of FIG. 17A is about 60 inches in length, and the gas removal flowpath of the system of FIG. 17B is about 15 inches in length.
Figure 18:
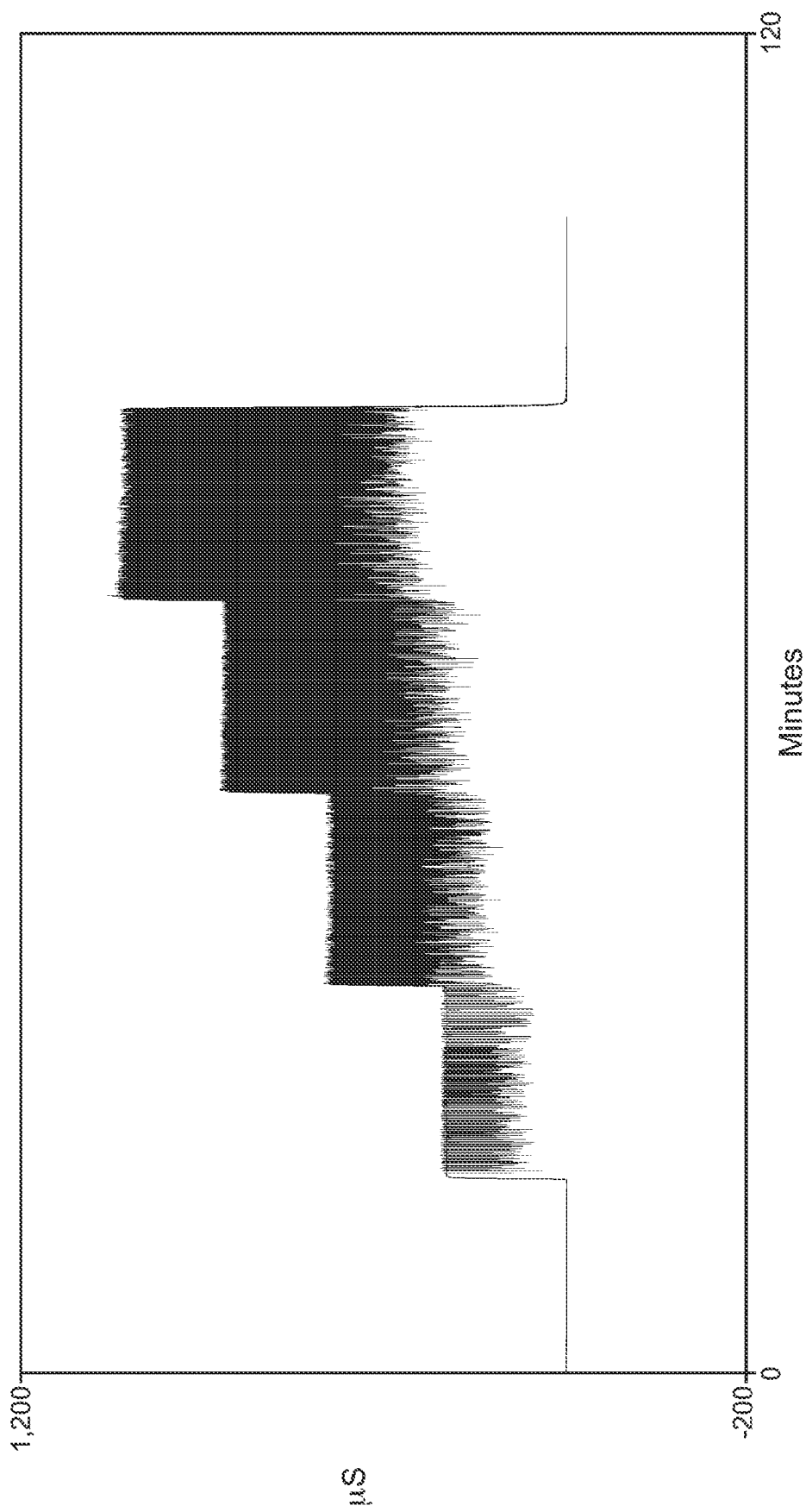
FIG. 18 shows the conductance of KOH eluents using the system of FIG. 1 without any gas removal device.

An ICS-2000 ion chromatography system (Dionex Corporation, Sunnyvale, Calif.) was used. A Dionex Chromeleon 6.8 chromatography data system was used for instrument control, data collection, and processing. The ICS-2000 system was fitted with a Dionex EGC KOH cartridge to generate KOH eluents electrolytically. The degas assembly was constructed according to FIGS. 13-14. A piece of Teflon AF2400 tubing (0.031-inch OD×0.008-inch ID×1.25-ft length) was used in the degas assembly. FIG. 17B shows the conductance of the KOH eluents generated at 1.0 mL/min. The results show that annular degasser described in this invention can be used to remove hydrogen gas produced by the electrolytic eluent generation process. FIG. 17A shows the conductance of the KOH eluents generated at 1.0 mL/min when the degas assembly was replaced with a conventional gas separation device such as that disclosed by the Liu patent. The results show that a good step-wise conductance profile may be achieved with the gas removal device and method of the present invention. By contrast, FIG. 18 shows the conductance of the KOH eluents when the system is used with the degas assembly removed. As shown in FIG. 18, the conductance profile of the KOH eluents is very noisy due to the presence of hydrogen gas bubbles in the eluent stream. In FIGS. 17A, 17B, and 18, the y-axis is micro-siemens and the x-axis is minutes.

For convenience in explanation and accurate definition in the appended claims, the terms "up" or "upper", "down" or "lower", "inside" or "inner", "outer" and "outside" are used to describe features of the present invention with reference to the positions of such features as displayed in the figures.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A degas assembly comprising:
   a low pressure fluid channel for carrying a wash fluid at a first pressure;
   a pressurized channel for carrying eluent including a gas at a second pressure higher than the first pressure;
   a degas separator defining a fluid barrier between the low pressure fluid channel and pressurized fluid channel, the separator configured to retain liquid in the pressurized fluid channel and allow gas to flow through the separator to the low pressure fluid channel;
   wherein the pressurized fluid channel extends along an outer periphery of the low pressure fluid channel, and the second pressure is at least about 1000 psi.

2. The degas assembly according to claim 1, the degas assembly comprises a central lumen extending within an outer tubing,
   wherein the central lumen forms the low pressure fluid channel, an annular space between the central lumen and the tubing defines the pressurized channel, and a wall of the central lumen defines the degas separator.

3. The degas assembly according to claim 1, wherein the pressurized fluid channel extends along substantially the entire outer periphery and substantially the entire length of the low pressure fluid channel.

4. The degas assembly according to claim 1, wherein the eluent is received from an eluent generator and has a pressure of at least about 3300 psi.

5. The degas assembly according to claim 1, wherein the eluent is received from an eluent generator and has a pressure between about 3300 psi and about 5000 psi.

6. The degas assembly according to claim 1, further comprising a low pressure channel member defining the low pressure fluid channel and a pressurized channel member defining the pressurized fluid channel, each of the channel members comprising inert polymer tubing.

7. The degas assembly according to claim 6, wherein the low pressure fluid channel member comprises amorphous fluoropolymer tubing.

8. The degas assembly according to claim 6, wherein the pressurized fluid channel member comprises reinforced polyetheretherketone (PEEK) tubing.

9. The degas assembly according to claim 1, further comprising:
   an inlet housing including:
      an eluent inlet for connecting to an eluent generator; and
      a wash inlet for connecting to a wash source; and
   an outlet housing including:
      an eluent outlet; and
      a wash outlet.

10. The degas assembly according to claim 9, wherein the low pressure fluid channel is fluidicly connected to the wash inlet and the wash outlet, and the pressurized fluid channel is fluidically connected to the eluent inlet and the eluent outlet.

11. The degas assembly according to claim 10, the low pressure fluid channel and pressurized fluid channel being substantially coaxial flexible tubes, wherein at least one of the low pressure and pressurized tubes includes a splined portion at an outlet end and clamped within the outlet housing, the splined portion configured to allow fluid to flow through the splines when the splined portion is clamped.

12. The degas assembly according to claim 11, wherein the splined portion extends along substantially the entire length of the pressurized tube.

13. The degas assembly according to claim 2, wherein the outer tubing has a non-circular cross-section.

14. The degas assembly according to claim 2, wherein an outer surface of the central lumen is non-cylindrical.

15. A liquid chromatography system comprising:
the degas assembly according to claim 10; and
a pressurized liquid chromatography column;
wherein eluent from the outlet housing flows to the column.

16. The system according to claim 15, further comprising a pump, wherein the degas assembly is positioned downstream from the pump.

17. The system according to claim 15, further comprising a pump, wherein the degas assembly is positioned upstream from an inlet of the pump.

18. A method of separating gas from an eluent for liquid chromatography, the method comprising:
flowing high pressure eluent to a degas assembly, the degas assembly including an inner flow channel and outer flow channel with a degas separator disposed therebetween, said degas separator being a permeable membrane;
flowing the eluent to the outer flow channel; and
separating gas from the eluent into the inner flow channel hut retaining liquid from the eluent in the outer flow channel via the degas separator;
wherein the high pressure eluent has a pressure of at least about 1000 psi.

19. The method according to claim 18, wherein the eluent includes gas resulting from electrolysis.

20. The method according to claim 18, further comprising directing the separated eluent from an outlet of the outer flow channel to a liquid chromatography column.

21. The method according to claim 18, further comprising flowing regenerant through the inner flow channel thereby flushing the separated gas.

22. The method according to claim 18, wherein the eluent is received from an eluent generator.

23. The method according to claim 22, wherein eluent from the eluent generator is at a pressure of at least about 3300 psi.

24. The method according to claim 22, wherein eluent from the eluent generator is at a pressure of between about 3300 psi and about 5000 psi.

25. The method according to claim 18, wherein the degas separator is a polymer tube.

26. The method according to claim 18, the outer flow channel at least partially enveloping the inner flow channel, wherein the flowing eluent to the outer flow channel is performed so as to place the inner flow channel in compression.

27. The degas assembly according to claim 1, the pressurized channel being in fluid communication with an eluent generator and at least one of a chromatography column and a suppressor, wherein the pressurized channel is located upstream from the at least one of a chromatography column and a suppressor.

28. The degas assembly according to claim 6, wherein the low pressure channel member includes at least one flared end, and the at least one flared end is configured to form a fluid seal when engaged with a fluid inlet or outlet port.

29. The degas assembly according to claim 28, wherein the at least one flared end is thermally formed.

30. The degas assembly according to claim 1, wherein the low pressure fluid channel is capped at one end.

31. A degas assembly comprising:
a low pressure fluid channel for carrying a wash fluid at a first pressure;
a pressurized channel for carrying eluent including a gas at a second pressure higher than the first pressure, the pressurized channel including an eluent inlet downstream from an eluent generator, and an eluent outlet located upstream from a sample injector; and
a degas separator defining a fluid barrier between the low pressure fluid channel and pressurized fluid channel, wherein the pressurized fluid channel extends along an outer periphery of the low pressure fluid channel;
wherein the degas separator retains liquid in the pressurized fluid channel and allow gas to flow through the separator to the low pressure fluid channel in order to remove gas from the eluent before the eluent reaches the sample injector.

* * * * *